(12) United States Patent
Goulet et al.

(10) Patent No.: US 12,208,092 B2
(45) Date of Patent: Jan. 28, 2025

(54) COMPOSITIONS AND METHODS FOR ADMINISTERING PALTUSOTINE TO PATIENTS WITH HEPATIC IMPAIRMENT

(71) Applicant: CRINETICS PHARMACEUTICALS, INC., San Diego, CA (US)

(72) Inventors: Lance Goulet, Poway, CA (US); William Humphreys, Lawrenceville, NJ (US); Ajay Madan, San Diego, CA (US); Sha Luo, San Diego, CA (US)

(73) Assignee: CRINETICS PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 18/615,512

(22) Filed: Mar. 25, 2024

(65) Prior Publication Data

US 2024/0325376 A1   Oct. 3, 2024

Related U.S. Application Data

(60) Provisional application No. 63/455,193, filed on Mar. 28, 2023.

(51) Int. Cl.
| | | |
|---|---|---|
| *A61K 31/4709* | (2006.01) | |
| *A61K 9/00* | (2006.01) | |
| *A61K 9/20* | (2006.01) | |
| *A61K 9/28* | (2006.01) | |

(52) U.S. Cl.
CPC ........ *A61K 31/4709* (2013.01); *A61K 9/0053* (2013.01); *A61K 9/2013* (2013.01); *A61K 9/2018* (2013.01); *A61K 9/2027* (2013.01); *A61K 9/2054* (2013.01); *A61K 9/2813* (2013.01); *A61K 9/2866* (2013.01)

(58) Field of Classification Search
None
See application file for complete search history.

(56) References Cited

U.S. PATENT DOCUMENTS

| | | |
|---|---|---|
| 9,896,432 B2 | 2/2018 | Zhao et al. |
| 10,351,547 B2 | 7/2019 | Zhao et al. |
| 10,464,918 B2 | 11/2019 | Reddy et al. |
| 10,597,377 B2 | 3/2020 | Zhao et al. |
| 10,875,839 B2 | 12/2020 | Zhao et al. |
| 10,889,561 B2 | 1/2021 | Reddy et al. |
| 11,266,641 B1 | 3/2022 | Burke et al. |
| 11,414,397 B2 | 8/2022 | Zhao et al. |
| 2015/0157575 A1 * | 6/2015 | Yang ............ A61K 9/205 514/254.09 |
| 2018/0016252 A1 | 1/2018 | Zhao et al. |
| 2019/0002431 A1 | 1/2019 | Zhao et al. |
| 2019/0218202 A1 | 7/2019 | Reddy et al. |
| 2019/0382367 A1 | 12/2019 | Zhao et al. |
| 2020/0048219 A1 | 2/2020 | Reddy et al. |
| 2020/0190053 A1 | 6/2020 | Zhao et al. |
| 2021/0087165 A1 | 3/2021 | Reddy et al. |
| 2021/0171492 A1 | 6/2021 | Zhao et al. |
| 2022/0071986 A1 | 3/2022 | Burke et al. |
| 2022/0143007 A1 | 5/2022 | Burke et al. |
| 2022/0267295 A1 | 8/2022 | Reddy et al. |
| 2022/0380337 A1 | 12/2022 | Zhao et al. |
| 2022/0387420 A1 | 12/2022 | Madan et al. |

OTHER PUBLICATIONS

Lagast et al. (Poster 21-A-127 presented at the North American Neuroendocrine Tumor Society NET Medical Symposium Nov. 4-6, 2021).*
Madan et al. (Endocrine Abstract, 70 AEP627, 2020).*
Delcò et al. (Drug Safety 2005; 28 (6): 529-545).*
Madan, et al.; Paltusotine, a novel oral once-daily nonpeptide SST2 receptor agonist, suppresses GH and IGF-1 in healthy volunteers; Pituitary, Apr. 2022;25(2):328-339. doi: 10.1007/s11102-021-01201-z. Epub Jan. 9, 2022.
Horsmans, et al., Effect of Hepatic Impairment on the Pharmacokinetics of Pasireotide (SOM230): Results From a Multicenter Phase I Study; J Clin Pharmacol; Apr. 2012;52(4):552-8. doi: 10.1177/0091270011400072.
Luo, et al.; SAT628 Effect Of Hepatic Impairment On The Pharmacokinetics, Safety, And Tolerability Of Oral Paltusotine, A Non-peptide, Selective Somatostatin Receptor Subtype 2 Agonist; J Endocr Soc. Oct. 5, 2023; 7(Suppl 1): bvad114.1361; Published online Oct. 5, 2023. doi: 10.1210/jendso/bvad114.1361.
Ottesen, et al.; The pharmacokinetics of octreotide in cirrhosis and in healthy man; J Hepatol. May 1997; 26(5):1018-25. doi: 10.1016/s0168-8278(97)80110-9.
USPTO, International Search Report & Written Opinion for PCT/US2024/021308, mailed on Jun. 3, 2024.
Gadelha, M., et al., ACROBAT Edge: Safety and Efficacy of Switching Injected SRLs to Oral Paltusotine in Patients With Acromegaly, J Clin Endocrinol Metab., May 2023; 108(5): e148-e159. Published online Nov. 10, 2022.; doi: 10.1210/clinem/dgac643.
Crinetics Pharmaceuticals, Inc., NCT03789656, An Study to Evaluate the Safety and Efficacy of Paltusotine for the Treatment of Acromegaly (ACROBAT Edge), ClinicalTrials.gov, Dec. 28, 2018.
Crinetics Pharmaceuticals, Inc., NCT03792555, A Study to Evaluate the Safety and Efficacy of Paltusotine for the Treatment of Acromegaly (ACROBAT Evolve), ClinicalTrials.gov, Jan. 3, 2019.

* cited by examiner

*Primary Examiner* — Bong-Sook Baek
(74) *Attorney, Agent, or Firm* — WILSON SONSINI GOODRICH & ROSATI

(57) ABSTRACT

Provided are compositions and methods for administering paltusotine, or a pharmaceutically acceptable salt thereof, to a patient having hepatic impairment.

27 Claims, 10 Drawing Sheets

COMPOSITIONS AND METHODS FOR ADMINISTERING PALTUSOTINE TO PATIENTS WITH HEPATIC IMPAIRMENT

CROSS-REFERENCE TO RELATED APPLICATIONS

This application claims the benefit of U.S. Provisional Patent Application No. 63/455,193, filed Mar. 28, 2023, which is incorporated herein in its entirety by reference.

FIELD

Provided are compositions and methods for administering paltusotine, or a pharmaceutically acceptable salt thereof, to a patient having hepatic impairment.

BACKGROUND

Somatostatin is a peptide hormone that regulates the endocrine system and affects neurotransmission and cell proliferation via interaction with G-protein-coupled somatostatin receptors and inhibition of the release of numerous secondary hormones. Six subtype somatostatin receptor proteins have been identified (SSTR1, SSTR2a, SSTR2b, SSTR3, SSTR4, SSTR5) and are encoded by five different somatostatin receptor genes. Modulation of a particular subtype somatostatin receptor, or combination thereof, is attractive for the treatment of conditions, diseases, or disorders that would benefit from modulating somatostatin activity.

Despite the advances that have been made in this field, there remains a need for new therapeutic products useful for treatment of conditions, diseases, or disorders that would benefit from modulating somatostatin activity. One such agent is paltusotine, which is an SST2 agonist that has the following chemical structure:

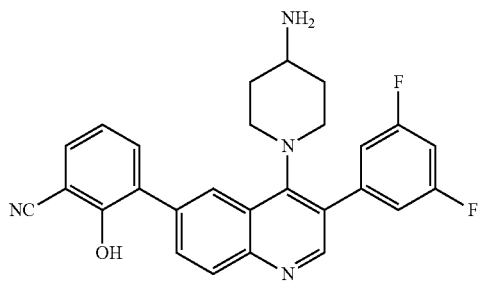 [SMILES: N#Cc1cccc(-c2ccc3ncc(-c4cc(F)cc(F)c4)c(N4CCC(N)CC4)c3c2)c1O]

Paltusotine is an orally administered nonpeptide somatostatin agonist currently undergoing clinical studies for the treatment of acromegaly and carcinoid syndrome.

Hepatic impairment is a condition wherein normal functioning of the liver is reduced. Hepatic impairment can be acute, with rapid onset, or chronic. Chronic hepatic impairment, or cirrhosis, can occur from many causes, such as excessive consumption of alcohol, hepatitis, autoimmune disease, heredity, or metabolism, or can be idiopathic. Liver damage is generally irreversible, and treatment consists of prevention of progression and treatment of symptoms. In severe cases, liver transplant is the only option. Hepatic impairment can exhibit no significant symptoms, or may be characterized by such symptoms as reduced ability for the blood to clot (coagulopathy) and brain dysfunction (encephalopathy), fluid retention in the abdominal cavity, increased infection risk, hypogonadism, change in liver size, jaundice, and increased sensitivity to medication.

The changes in systemic drug exposures, as quantified by pharmacokinetic parameters such as AUC, $C_{max}$, and $t_{1/2}$ of a drug and/or its metabolites, in patients with hepatic impairment can lead to many problems, including need for adjusting dose, need for liver function tests, complications for physicians in prescribing due to lack of availability of suitable doses and/or lack of availability of certain medications to those with hepatic impairment, and unintended overdosing.

There is a significant, unmet need for methods for administering a SST2 agonist, such as paltusotine, or a pharmaceutically acceptable salt thereof, to a patient in need thereof, wherein the patient has hepatic impairment. The present disclosure fulfills these and other needs, evident in reference to the following disclosure.

BRIEF SUMMARY

Provided is a method of administering paltusotine, or a pharmaceutically acceptable salt thereof, to a patient, wherein the patient has hepatic impairment.

Also provided is method of administering a therapeutically effective amount of paltusotine, or a pharmaceutically acceptable salt thereof, to a patient, wherein the patient has hepatic impairment, and wherein the therapeutically effective amount of paltusotine, or a pharmaceutically acceptable salt thereof, is the same amount that would be administered to a patient who does not have hepatic impairment.

Also provided is a method of administering to a patient a therapeutically effective amount of paltusotine, or a pharmaceutically acceptable salt thereof; subsequently determining that the patient has hepatic impairment; and administering the same therapeutically effective amount of paltusotine, or a pharmaceutically acceptable salt thereof, to the patient.

Also provided is a pharmaceutical composition for use in treating a patient with paltusotine, wherein the patient has hepatic impairment, wherein the composition includes paltusotine, or a pharmaceutically acceptable salt thereof.

Also provided is a pharmaceutical composition for use in treating a patient with paltusotine, wherein the patient has hepatic impairment, wherein the composition includes a therapeutically effective amount of paltusotine, or a pharmaceutically acceptable salt thereof, wherein the composition includes the same amount of paltusotine, or a pharmaceutically acceptable salt thereof, for use in treating a patient with paltusotine who does not have hepatic impairment.

Also included is a use of paltusotine, or a pharmaceutically acceptable salt thereof, in the manufacture of a medicament for treating a patient with hepatic impairment.

Also included is paltusotine, or a pharmaceutically acceptable salt thereof, for use in a method of treating a patient, said method comprises administering a therapeutically effective amount of paltusotine, or a pharmaceutically acceptable salt thereof, to the patient; subsequently determining that the patient has hepatic impairment; and administering the same therapeutically effective amount of paltusotine, or a pharmaceutically acceptable salt thereof, to the patient.

BRIEF DESCRIPTION OF THE DRAWINGS

FIG. 3A depicts the mean plasma concentration of paltusotine versus time of patients with mild hepatic impairment; FIG. 3B depicts the mean plasma concentration of paltusotine versus time of patients with moderate hepatic impairment; FIG. 3C depicts the mean plasma concentration of paltusotine versus time of patients with severe hepatic impairment; and FIG. 3D depicts the mean plasma concentration of paltusotine versus time of patients without hepatic impairment (i.e. normal patients).

DETAILED DESCRIPTION

Figure 1:
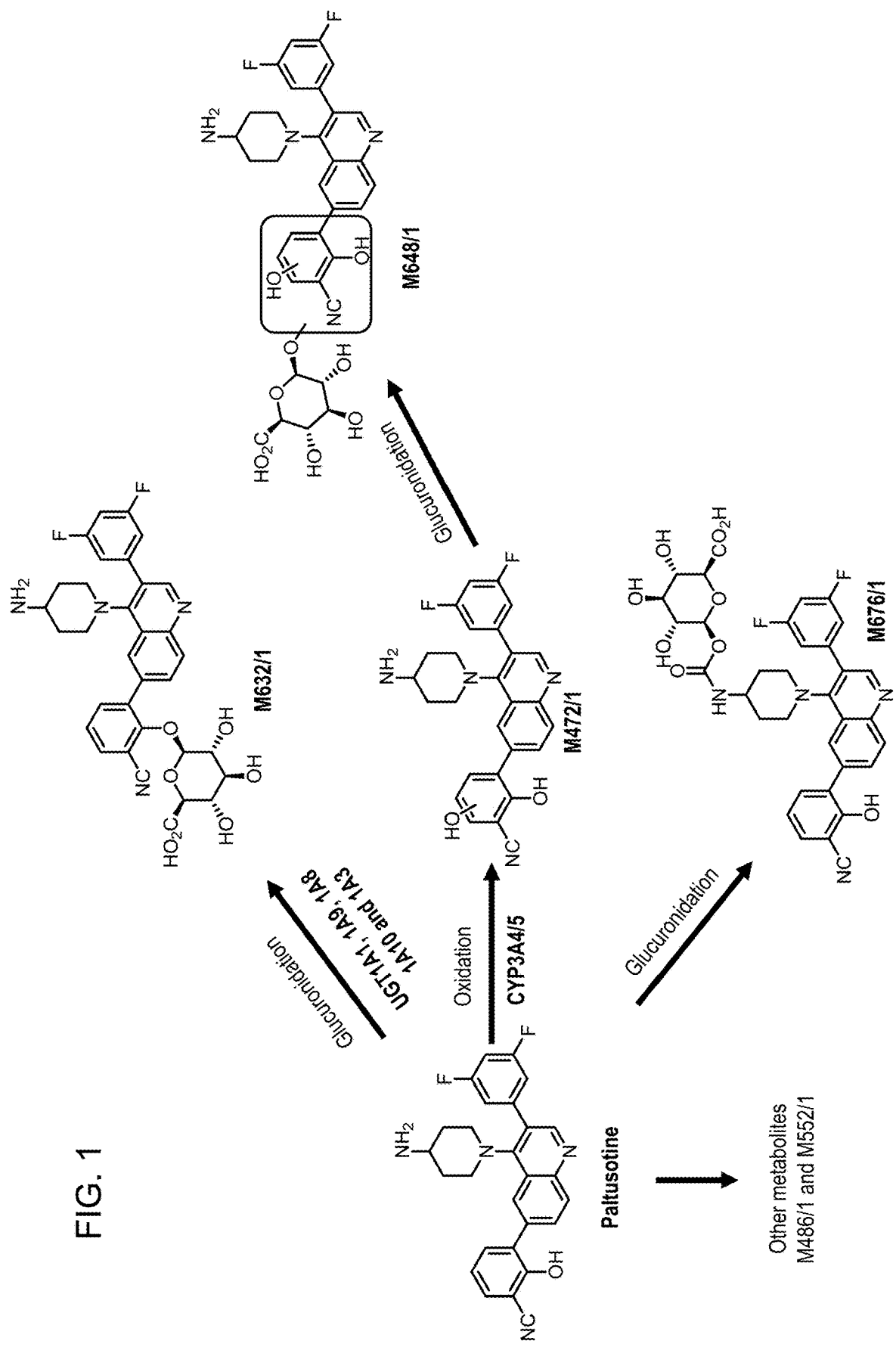
FIG. 1 depicts paltusotine metabolites detected in human excreta after administration of [$^{14}$C]paltusotine.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as "comprises" and "comprising" are to be construed in an open, inclusive sense, that is, as "including, but not limited to." Further, headings provided herein are for convenience only and do not interpret the scope or meaning of the claimed invention.

References throughout this specification to "one embodiment" or "an embodiment" or "some embodiments" or "a certain embodiment" means that a particular feature, structure, or characteristic described in connection with the embodiment is included in at least one embodiment. Thus, the appearances of the phrases "in one embodiment" or "in an embodiment" or "in some embodiments" or "in a certain embodiment" in various places throughout this specification are not necessarily all referring to the same embodiment.

Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise.

As used herein, "paltusotine" may be referred to as paltusotine free base, paltusotine.HCl, 3-[4-(4-amino-1-piperidyl)-3-(3,5-difluorophenyl)-6-quinolyl]-2-hydroxybenzonitrile, 3-[4-(4-amino-1-piperidyl)-3-(3,5-difluorophenyl)-6-quinolyl]-2-hydroxybenzonitrile hydrochloride, 3-[4-(4-amino-1-piperidyl)-3-(3,5-difluorophenyl)-6-quinolyl]-2-hydroxybenzonitrile monohydrochloride, and 3-[4-(4-amino-1-piperidyl)-3-(3,5-difluorophenyl)-6-quinolyl]-2-hydroxybenzonitrile dihydrochloride. Additional paltusotine salts are disclosed in U.S. Patent Application Publication U.S. Patent Application Publication No. 2022/0267295, the entire contents of which is incorporated by reference.

As used herein, "hepatic impairment" means hepatocellular (liver) dysfunction.

As used herein, "Child-Pugh Score" is a score based on five clinical measures of hepatic impairment, including levels of bilirubin, serum albumin, prothrombin time international normalized ratio (PT INR), ascites, and hepatic encephalopathy. Each measure is given a ranking of 1, 2, or 3, and the sum of the five rankings is the Child-Pugh Score. The Child-Pugh Score can be used to classify hepatic impairment by placing subjects in a Child-Pugh Group.

As used herein, "mild hepatic impairment" refers to a ranking level of hepatic impairment based on a Child-Pugh Score of 5-6.

As used herein, "moderate hepatic impairment" refers to a ranking level of hepatic impairment based on a Child-Pugh Score of 7-9.

As used herein, "severe hepatic impairment" refers to a ranking level of hepatic impairment based on a Child-Pugh Score of 10-15.

As used herein, "about" means ±10% of the stated value, and includes more specifically values of ±5%, ±2%, and ±1% of the stated value.

As used herein, "AUC" refers to the area under the curve, or the integral, of the plasma concentration of paltusotine, or a pharmaceutically acceptable salt thereof, over time following a dosing event.

As used herein, "$AUC_{0-t}$" refers to the area under the curve of the plasma concentration of paltusotine, or a pharmaceutically acceptable salt thereof, versus time from 0 to the last quantifiable concentration.

As used herein, "$AUC_{0-24}$" refers to the area under the curve of the plasma concentration of paltusotine, or a pharmaceutically acceptable salt thereof, versus time from 0 extrapolated to 24 hours.

As used herein, "$AUC_{0-\infty}$" or "$AUC_{0-inf}$" refers to the area under the curve of the plasma concentration of paltusotine, or a pharmaceutically acceptable salt thereof, versus time from 0 to infinity.

As used herein, "$C_{max}$" is a pharmacokinetic parameter denoting the maximum observed blood plasma concentration following delivery of paltusotine, or a pharmaceutically acceptable salt thereof.

As used herein, "$t_{max}$" refers to the time to $C_{max}$ following delivery of paltusotine, or a pharmaceutically acceptable salt thereof.

As used herein, "$t_{lag}$" refers to the time delay between the time of dosing of paltusotine, or a pharmaceutically acceptable salt thereof, and the time of the appearance of the measurable test article.

As used herein, "$t_{1/2}$" or "plasma half-life" or "elimination half-life" or the like refers to the apparent terminal phase half-life following delivery of paltusotine, or a pharmaceutically acceptable salt thereof.

As used herein, "MRT" refers to the apparent mean residence time of paltusotine, or a pharmaceutically acceptable salt thereof.

As used herein, "CL/F" refers to the apparent total body clearance of paltusotine, or a pharmaceutically acceptable salt thereof.

As used herein, "$V_z/F$" refers to the apparent volume of distribution of paltusotine, or a pharmaceutically acceptable salt thereof.

As used herein, "$\lambda_z$" refers to the apparent terminal rate constant.

As used herein, "BMI" refers to the body mass index of a patient.

As used herein, "ECG" refers to electrocardiogram.

As used herein, "QTcF" refers to QT interval corrected using Fridericia's formula.

As used herein, "IGF-1" refers to insulin-like growth factor 1.

As used herein, "AE" refers to adverse event and "TEAE" refers to treatment emergent adverse event.

As used herein, "PK" refers to pharmacokinetic(s) and "PD" refers to pharmacodynamic(s).

As used herein, "GH" refers to growth hormone.

As used herein, "administering to a patient" refers to the process of introducing a composition or dosage form into the patient via an art-recognized means of introduction.

As used herein, "adjusting administration", "altering administration", "adjusting dosing", or "altering dosing" are all equivalent and mean tapering off, reducing or increasing the dose of the substance or ceasing to administer the substance to the patient.

As used herein the term "disorder" is intended to be generally synonymous, and is used interchangeably with the terms "disease," "syndrome," and "condition" (as in medical condition), in that all reflect an abnormal condition of the human or animal body or of one of its parts that impairs normal functioning, and is typically manifested by distinguishing signs and symptoms.

As used herein, a "dose" means the measured quantity of an active agent to be taken at one time by a patient. In certain embodiments, wherein the active agent is not paltusotine free base, the quantity is the molar equivalent to the corresponding amount of paltusotine free base. For example, often a drug is packaged in a pharmaceutically acceptable salt form, for instance paltusotine monohydrochloride, and the dosage form strength refers to the mass of the molar equivalent of the corresponding free base, paltusotine. As an example, 21.6 mg of paltusotine monohydrochloride is the molar equivalent of 20 mg of paltusotine free base.

As used herein, "effective amount" and "therapeutically effective amount" of an agent, compound, drug, or composition is an amount which is nontoxic and effective for producing some desired therapeutic effect upon administration to a subject or patient (e.g., a human subject or patient). The precise therapeutically effective amount for a subject may depend upon, e.g., the subject's size and health, the nature and extent of the condition, the therapeutics or combination of therapeutics selected for administration, and other variables known to those of skill in the art. The effective amount for a given situation is determined by routine experimentation and is within the judgment of the clinician.

As used herein, "patient" or "individual" or "subject" means a mammal, including a human, for whom or which therapy is desired, and generally refers to the recipient of the therapy.

As used herein, "pharmaceutically acceptable" refers to a material that is not biologically or otherwise undesirable, i.e., the material may be incorporated into a pharmaceutical composition to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" (or "active") derivative or analog, refers to a derivative or analog having the same type of pharmacological activity as the parent compound and approximately equivalent in degree. The term "pharmaceutically acceptable salts" include acid addition salts which are formed with suitable inorganic acids, inorganic bases, or organic bases.

As used herein, "risk" means the probability or chance of adverse reaction, injury, or other undesirable outcome arising from a medical treatment. An "acceptable risk" means a measure of the risk of harm, injury, or disease arising from a medical treatment that will be tolerated by an individual or group. Whether a risk is "acceptable" will depend upon the advantages that the individual or group perceives to be obtainable in return for taking the risk, whether they accept whatever scientific and other advice is offered about the magnitude of the risk, and numerous other factors, both political and social. An "acceptable risk" of an adverse reaction means that an individual or a group in society is willing to take or be subjected to the risk that the adverse reaction might occur since the adverse reaction is one whose probability of occurrence is small, or whose consequences are so slight, or the benefits (perceived or real) of the active agent are so great. An "unacceptable risk" of an adverse reaction means that an individual or a group in society is unwilling to take or be subjected to the risk that the adverse reaction might occur upon weighing the probability of occurrence of the adverse reaction, the consequences of the adverse reaction, and the benefits (perceived or real) of the active agent. "At risk" means in a state or condition marked by a high level of risk or susceptibility. Risk assessment consists of identifying and characterizing the nature, frequency, and severity of the risks associated with the use of a product.

As used herein, "safety" means the incidence or severity of adverse events associated with administration of an active agent, including adverse effects associated with patient-related factors (e.g., age, gender, ethnicity, race, target illness, abnormalities of renal or hepatic function, co-morbid illnesses, genetic characteristics such as metabolic status, or environment) and active agent-related factors (e.g., dose, plasma level, duration of exposure, or concomitant medication).

As used herein, "treating" or "treatment" refers to therapeutic applications to slow or stop progression of a disorder, and/or alleviate symptoms thereof.

Methods of Treatment

Provided is a method of administering paltusotine, or a pharmaceutically acceptable salt thereof, to a patient, wherein the patient has hepatic impairment, comprising administering to the patient paltusotine free base or a pharmaceutically acceptable salt thereof.

In certain embodiments, the paltusotine, or a pharmaceutically acceptable salt thereof, is administered in a therapeutically effective amount.

Also provided is a method of administering paltusotine, or a pharmaceutically acceptable salt thereof, to a patient, wherein the patient has hepatic impairment, comprising: administering a therapeutically effective amount of paltusotine, or a pharmaceutically acceptable salt thereof, to the patient having hepatic impairment, wherein the therapeutically effective amount is the same amount that would be administered to a patient who does not have hepatic impairment.

Also provided is a method administering paltusotine, or a pharmaceutically acceptable salt thereof, to a patient comprising: administering to the patient a therapeutically effective amount of paltusotine, or a pharmaceutically acceptable salt thereof; subsequently determining that the patient has hepatic impairment; and administering the same therapeutically effective amount of paltusotine, or a pharmaceutically acceptable salt thereof.

In certain embodiments, the patient with hepatic impairment has equivalent exposure of paltusotine free base as in a patient with normal hepatic function who is administered the same amount of the paltusotine, or a pharmaceutically acceptable salt thereof.

In certain embodiments, the patient has mild, moderate, or severe hepatic impairment.

In certain embodiments, the patient has a Child-Pugh Score of 5-6, 7-9, or 10-15.

In certain embodiments, the patient has mild hepatic impairment.

In certain embodiments, the patient has a Child-Pugh Score of 5-6.

In certain embodiments, the patient has moderate hepatic impairment.

In certain embodiments, the patient has a Child-Pugh Score of 7-9.

In certain embodiments, the patient has severe hepatic impairment.

In certain embodiments, the patient has a Child-Pugh Score of 10-15.

In certain embodiments, the paltusotine, or a pharmaceutically acceptable salt thereof, is administered in an amount equivalent to about 10 mg to about 120 mg of paltusotine free base. In certain embodiments, the paltusotine, or a pharmaceutically acceptable salt thereof, is administered in an amount equivalent to about 40 mg to about 120 mg of paltusotine free base. In certain embodiments, the paltusotine, or a pharmaceutically acceptable salt thereof, is administered in an amount equivalent to about 40 mg to about 60 mg of paltusotine free base.

In certain embodiments, the paltusotine, or a pharmaceutically acceptable salt thereof, is administered in an amount equivalent to about 10 mg, about 20 mg, about 30 mg, about 40 mg, about 50 mg, about 60 mg, about 70 mg, about 80 mg, about 90 mg, about 100 mg, about 110 mg, or about 120 mg of paltusotine free base.

In certain embodiments, the patient has acromegaly, carcinoid syndrome and/or neuroendocrine tumor(s) (NETs).

In certain embodiments, the paltusotine, or a pharmaceutically acceptable salt thereof, is administered to the patient to treat acromegaly, carcinoid syndrome and/or NETs.

In certain embodiments, the patient has acromegaly.

In certain embodiments, the patient has acromegaly and the paltusotine, or a pharmaceutically acceptable salt thereof, is administered in an amount equivalent to about 40 mg to about 60 mg of paltusotine free base. In certain embodiments, the patient has acromegaly and the paltusotine, or a pharmaceutically acceptable salt thereof, is administered in an amount equivalent to about 40 mg of paltusotine free base. In certain embodiments, the patient has acromegaly and the paltusotine, or a pharmaceutically acceptable salt thereof, is administered in an amount equivalent to about 60 mg of paltusotine free base.

In certain embodiments the patient has acromegaly and the paltusotine, or a pharmaceutically acceptable salt thereof, is administered to the patient to treat acromegaly.

In certain embodiments, the patient has carcinoid syndrome and/or NETs. In certain embodiments the patient has carcinoid syndrome.

In certain embodiments, the patient has carcinoid syndrome and/or NETs and the paltusotine, or a pharmaceutically acceptable salt thereof, is administered in an amount equivalent to about 40 mg to about 120 mg of paltusotine free base. In certain embodiments, the patient has carcinoid syndrome and/or NETs and the paltusotine, or a pharmaceutically acceptable salt thereof, is administered in an amount equivalent to about 40 mg of paltusotine free base. In certain embodiments, the patient has carcinoid syndrome and/or NETs and the paltusotine, or a pharmaceutically acceptable salt thereof, is administered in an amount equivalent to about 60 mg of paltusotine free base. In certain embodiments, the patient has carcinoid syndrome and/or NETs and the paltusotine, or a pharmaceutically acceptable salt thereof, is administered in an amount equivalent to about 80 mg of paltusotine free base. In certain embodiments, the patient has carcinoid syndrome and/or NETs and the paltusotine, or a pharmaceutically acceptable salt thereof, is administered in an amount equivalent to about 100 mg of paltusotine free base. In certain embodiments, the patient has carcinoid syndrome and/or NETs and the paltusotine, or a pharmaceutically acceptable salt thereof, is administered in an amount equivalent to about 120 mg of paltusotine free base.

In certain embodiments the patient has carcinoid syndrome and/or NETs and the paltusotine, or a pharmaceutically acceptable salt thereof, is administered to the patient to treat carcinoid syndrome and/or NETs. In certain embodiments the patient has carcinoid syndrome and the paltusotine, or a pharmaceutically acceptable salt thereof, is administered to the patient to treat carcinoid syndrome.

In certain embodiments, the paltusotine, or a pharmaceutically acceptable salt thereof, is administered in one or more dosage forms. In certain embodiments, the paltusotine, or a pharmaceutically acceptable salt thereof, is administered in two or more dosage forms. In certain embodiments, the paltusotine, or a pharmaceutically acceptable salt thereof, is administered in three or more dosage forms. In certain embodiments, the paltusotine, or a pharmaceutically acceptable salt thereof, is administered in four or more dosage forms. In certain embodiments, the paltusotine, or a pharmaceutically acceptable salt thereof, is administered in five or more dosage forms.

In certain embodiments, the dosage form comprises an amount of paltusotine equivalent to about 20 mg, about 30 mg, about 40 mg, about 50 mg, about 60 mg, or about 80 mg of paltusotine free base. In certain embodiments, the dosage form comprises an amount of paltusotine equivalent to about 20 mg of paltusotine free base. In certain embodiments, the dosage form comprises an amount of paltusotine equivalent to about 30 mg of paltusotine free base. In certain embodiments, the dosage form comprises an amount of paltusotine equivalent to about 40 mg of paltusotine free base. In certain embodiments, the dosage form comprises an amount of paltusotine equivalent to about 50 mg of paltusotine free base. In certain embodiments, the dosage form comprises an amount of paltusotine equivalent to about 60 mg of paltusotine free base. In certain embodiments, the dosage form comprises an amount of paltusotine equivalent to about 80 mg of paltusotine free base.

In certain embodiments, the paltusotine, or a pharmaceutically acceptable salt thereof, is administered in one dosage form comprising an amount of paltusotine equivalent to about 40 mg, about 60 mg, or about 80 mg of paltusotine free base. In certain embodiments, the paltusotine, or a pharmaceutically acceptable salt thereof, is administered in two dosage forms and each dosage form comprises an amount of paltusotine equivalent to about 20 mg, about 30 mg, about 40 mg, about 50 mg, or about 60 mg of paltusotine free base. In certain embodiments, the paltusotine, or a pharmaceutically acceptable salt thereof, is administered in three dosage forms and each dosage form comprises an amount of paltusotine equivalent to about 20 mg or about 40 mg of paltusotine free base. In certain embodiments, the paltusotine, or a pharmaceutically acceptable salt thereof, is administered in four dosage forms and each dosage form comprises an amount of paltusotine equivalent to about 20 mg or about 30 mg of paltusotine free base. In certain embodiments, the paltusotine, or a pharmaceutically acceptable salt thereof, is administered in five dosage forms and each dosage form comprises an amount of paltusotine equivalent to about 20 mg of paltusotine free base. In certain embodiments, the paltusotine, or a pharmaceutically acceptable salt thereof, is administered in six dosage forms and each dosage form comprises an amount of paltusotine equivalent to about 20 mg of paltusotine free base.

In certain embodiments, the paltusotine, or a pharmaceutically acceptable salt thereof, is administered orally. In certain embodiments, the paltusotine, or a pharmaceutically acceptable salt thereof, is administered orally via an oral dosage form. Oral dosage forms include tablets. In certain embodiments, the paltusotine, or a pharmaceutically acceptable salt thereof, is administered orally via the oral dosage form of a tablet.

In certain embodiments, the paltusotine, or a pharmaceutically acceptable salt thereof, is the hydrochloride salt of paltusotine. In certain embodiments, the hydrochloride salt of paltusotine is the monohydrochloride salt or the dihydrochloride salt. In a preferred embodiment, the hydrochloride salt of paltusotine is the monohydrochloride salt.

In certain embodiments, the hydrochloride salt of paltusotine is amorphous.

In certain embodiments, the paltusotine, or a pharmaceutically acceptable salt thereof, is administered daily. In certain embodiments, the paltusotine, or a pharmaceutically acceptable salt thereof, is administered once daily.

Pharmaceutical Compositions

Also provided is a pharmaceutical composition for use in treating a patient with paltusotine, wherein the patient has hepatic impairment, characterized in that the composition comprises paltusotine or a pharmaceutically acceptable salt thereof.

In certain embodiments, the composition contains a therapeutically effective amount of paltusotine or a pharmaceutically acceptable salt thereof.

Also provided is a pharmaceutical composition for use in treating a patient with paltusotine, wherein the patient has hepatic impairment, wherein the composition comprises a therapeutically effective amount of paltusotine, or a pharmaceutically acceptable salt thereof, characterized in that the composition contains the same amount of paltusotine, or a pharmaceutically acceptable salt thereof, that would be included in a composition for use in treating a patient with paltusotine who does not have hepatic impairment.

Also provided is paltusotine, or a pharmaceutically acceptable salt thereof, for use in a method of treating a patient, said method comprising: administering a therapeutically effective amount of paltusotine, or a pharmaceutically acceptable salt thereof, to the patient; subsequently determining that the patient has hepatic impairment; and administering the same therapeutically effective amount of paltusotine, or a pharmaceutically acceptable salt thereof, to the patient.

Also provided is a use of paltusotine, or a pharmaceutically acceptable salt thereof, in the manufacture of a medicament for treatment of a patient, wherein the patient has hepatic impairment.

In certain embodiments, the pharmaceutical composition provides equivalent exposure of paltusotine free base to the patient with hepatic impairment as compared to a patient with normal hepatic function who is administered the same composition.

In certain embodiments, the patient has mild, moderate, or severe hepatic impairment.

In certain embodiments, the patient has a Child-Pugh Score of 5-6, 7-9, or 10-15.

In certain embodiments, the patient has mild hepatic impairment.

In certain embodiments, the patient has a Child-Pugh Score of 5-6.

In certain embodiments, the patient has moderate hepatic impairment.

In certain embodiments, the patient has a Child-Pugh Score of 7-9.

In certain embodiments, the patient has severe hepatic impairment.

In certain embodiments, the patient has a Child-Pugh Score of 10-15.

In certain embodiments, the pharmaceutical composition contains an amount of paltusotine, or a pharmaceutically acceptable salt thereof, equivalent to about 10 mg to about 120 mg of paltusotine free base. In certain embodiments, the pharmaceutical composition contains an amount of paltusotine, or a pharmaceutically acceptable salt thereof, equivalent to about 40 mg to about 120 mg of paltusotine free base. In certain embodiments, the pharmaceutical composition contains an amount of paltusotine, or a pharmaceutically acceptable salt thereof, equivalent to about 40 mg to about 60 mg of paltusotine free base.

In certain embodiments, the pharmaceutical composition contains an amount of paltusotine, or a pharmaceutically acceptable salt thereof, equivalent to about 10 mg, about 20 mg, about 30 mg, about 40 mg, about 50 mg, about 60 mg, about 70 mg, about 80 mg, about 90 mg, about 100 mg, about 110 mg, or about 120 mg of paltusotine free base.

In certain embodiments, the patient has acromegaly, carcinoid syndrome and/or NETs.

In certain embodiments, the pharmaceutical composition is for use in treating acromegaly, carcinoid syndrome and/or NETs.

In certain embodiments, the patient has acromegaly.

In certain embodiments, the patient has acromegaly and the pharmaceutical composition contains an amount of paltusotine, or a pharmaceutically acceptable salt thereof, equivalent to about 40 mg to about 60 mg of paltusotine free base. In certain embodiments, the patient has acromegaly and the pharmaceutical composition contains an amount of paltusotine, or a pharmaceutically acceptable salt thereof, equivalent to about 40 mg of paltusotine free base. In certain embodiments, the patient has acromegaly and the pharmaceutical composition contains an amount of paltusotine, or a pharmaceutically acceptable salt thereof, equivalent to about 60 mg of paltusotine free base.

In certain embodiments, the pharmaceutical composition is for use in treating a patient with acromegaly.

In certain embodiments, the patient has carcinoid syndrome and/or NETs. In certain embodiments the patient has carcinoid syndrome.

In certain embodiments, the patient has carcinoid syndrome and/or NETs and the pharmaceutical composition contains an amount of paltusotine, or a pharmaceutically acceptable salt thereof, equivalent to about 40 mg to about 120 mg of paltusotine free base. In certain embodiments, the patient has carcinoid syndrome and/or NETs and the pharmaceutical composition contains an amount of paltusotine, or a pharmaceutically acceptable salt thereof, equivalent to about 40 mg of paltusotine free base. In certain embodiments, the patient has carcinoid syndrome and/or NETs and the pharmaceutical composition contains an amount of paltusotine, or a pharmaceutically acceptable salt thereof, equivalent to about 60 mg of paltusotine free base. In certain embodiments, the patient has carcinoid syndrome and/or NETs and the pharmaceutical composition contains an amount of paltusotine, or a pharmaceutically acceptable salt thereof, equivalent to about 80 mg of paltusotine free base. In certain embodiments, the patient has carcinoid syndrome and/or NETs and the pharmaceutical composition contains an amount of paltusotine, or a pharmaceutically acceptable salt thereof, equivalent to about 100 mg of paltusotine free base. In certain embodiments, the patient has carcinoid syndrome and/or NETs and the pharmaceutical composition contains an amount of paltusotine, or a pharmaceutically acceptable salt thereof, equivalent to about 120 mg of paltusotine free base.

In certain embodiments the patient has carcinoid syndrome and/or NETs and the pharmaceutical composition is for use in treating carcinoid syndrome and/or NETs. In certain embodiments the patient has carcinoid syndrome and the pharmaceutical composition is for use in treating carcinoid syndrome.

In certain embodiments, the pharmaceutical composition is formulated as an oral dosage form. Oral dosage forms include tablets. In certain embodiments, the pharmaceutical composition is a tablet.

In certain embodiments, the pharmaceutical compositions provided herein may be provided in unit dosage or multiple-dosage forms. Unit-dosage forms, as used herein, refer to physically discrete units suitable for administration to subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include individually packaged tablets. Unit dosage forms may be administered in fractions or multiples thereof. A multiple-dosage form is a plurality of identical unit-dosage forms packaged in a single container to be administered in segregated unit-dosage form. Examples of multiple-dosage forms include bottles of tablets.

In certain embodiments, the unit dosage form comprises an amount of paltusotine equivalent to about 20 mg, about 30 mg, about 40 mg, about 50 mg, about 60 mg, or about 80 mg of paltusotine free base. In certain embodiments, the unit dosage form comprises an amount of paltusotine equivalent to about 20 mg of paltusotine free base. In certain embodiments, the unit dosage form comprises an amount of paltusotine equivalent to about 30 mg of paltusotine free base. In certain embodiments, the unit dosage form comprises an amount of paltusotine equivalent to about 40 mg of paltusotine free base. In certain embodiments, the unit dosage form comprises an amount of paltusotine equivalent to about 50 mg of paltusotine free base. In certain embodiments, the unit dosage form comprises an amount of paltusotine equivalent to about 60 mg of paltusotine free base. In certain embodiments, the unit dosage form comprises an amount of paltusotine equivalent to about 80 mg of paltusotine free base.

In certain embodiments, the paltusotine, or a pharmaceutically acceptable salt thereof, is a hydrochloride salt of paltusotine. In certain embodiments, the hydrochloride salt of paltusotine is the monohydrochloride salt or the dihydrochloride salt. In a preferred embodiment, the hydrochloride salt of paltusotine is the monohydrochloride salt.

In certain embodiments, the hydrochloride salt of paltusotine is amorphous.

In certain embodiments, the pharmaceutical composition is administered daily. In certain embodiments, the pharmaceutical composition is administered once daily.

In certain embodiments, the pharmaceutical composition further comprises one or more pharmaceutically acceptable carriers or excipients. Pharmaceutically acceptable carriers or excipients include, but are not limited to, binders, fillers, diluents, disintegrants, wetting agents, lubricants, glidants, coloring agents, dye-migration inhibitors, sweetening agents, and flavoring agents.

Paltusotine

Paltusotine is an orally administered nonpeptide SST2 agonist having the structure shown below:

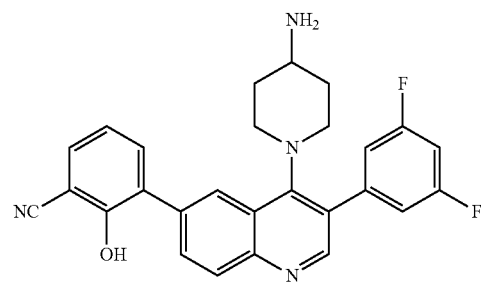 [SMILES: N#Cc1cccc(-c2ccc3ncc(-c4cc(F)cc(F)c4)c(N4CCC(N)CC4)c3c2)c1O]

In vitro, paltusotine inhibits cyclic adenosine monophosphate (cAMP) accumulation via human somatostatin receptor 2 (SST2) activation with an average drug (agonist) concentration that results in half-maximal response ($EC_{50}$) of 0.25 nmol/L, with selectivity over other human somatostatin receptors of >4000-fold. Paltusotine is >2000-fold selective for SST2 over a large panel of other known receptors, channels, and enzymes known to be targets of other drugs, thus reducing the risk of unwanted off-target activities or toxicities. Paltusotine exhibited a 75-fold bias for G-protein activation and subsequent lowering of intracellular cAMP levels, compared to β-arrestin activation and subsequent receptor internalization. This 75-fold bias suggests a reduced likelihood of desensitization of the receptor by paltusotine at pharmacologically relevant concentrations, potentially reducing the risk of tachyphylaxis.

The in vivo pharmacological efficacy of paltusotine has been examined in rat and dog. In the rat, acute efficacy was evaluated by examining the suppression of plasma GH in response to a challenge with rat growth hormone releasing hormone (rGHRH). Orally administered paltusotine significantly and dose dependently suppressed GH relative to vehicle-treated rats at doses ≥3 mg/kg. The plasma $EC_{50}$ for GH suppression was estimated to be 11 ng/mL. The effects of chronic, oral, 14-day administration of paltusotine were evaluated by measuring the sustained suppression of IGF-1 in the rat. Paltusotine (>10 mg/kg/day) was efficacious in suppressing plasma IGF-1 for up to 14 days. At the 10 mg/kg/day dose in the rat, the day-last mean plasma $C_{max}$ and $AUC_{0-24}$ of paltusotine were 127 ng/mL and 975 ng×h/mL, respectively. Octreotide, an injectable peptide SST2 agonist that is approved for the treatment of acromegaly, was evaluated as a positive control in the rat studies and demonstrated maximal effects similar to orally administered paltusotine. The sustained effect of paltusotine on suppression of IGF-1 was also demonstrated in Beagle dogs at oral doses ≥6 mg/kg/day for 7 days. The oral efficacy of paltusotine in vivo provides a strong rationale for its use as an oral treatment for acromegaly.

The synthesis of paltusotine is disclosed in U.S. Pat. No. 10,597,377, the entire contents of which are incorporated by reference.

Acromegaly

Acromegaly is a serious disease generally caused by a benign growth hormone (GH) secreting tumor in the pituitary with a reported prevalence in the U.S. of up to 8.8 per 100,000. The excess GH secretion causes increased secretion of insulin-like growth factor-1 (IGF-1) from the liver, which causes bone and cartilage overgrowth, organ enlargement, and changes in glucose and lipid metabolism. The symptoms of acromegaly include abnormal growth of hands and feet and changes in shape of the bone and cartilage that result in alteration of facial features. Overgrowth of bone and cartilage and thickening of tissue leads to arthritis, carpal tunnel syndrome, joint aches, enlarged lips, nose, and tongue, deepening of voice due to enlarged vocal cords, sleep apnea due to obstruction of airways, and enlargement of heart, liver, and other organs. Additional symptoms include thick, coarse, oily skin, skin tags, excessive sweating, and skin odor, fatigue and weakness, headaches, impaired vision, goiter, decreased libido, menstrual abnormalities in women, and erectile dysfunction in men.

The major treatment goals for acromegaly are to normalize serum GH and IGF-1 in order to reduce mortality, reverse or attenuate signs and symptoms, control tumor mass, and maintain pituitary function. Surgical removal of pituitary adenomas, if possible, is the preferred initial treatment for most acromegaly patients. Pharmacological treatments are used for patients who are not candidates for surgical removal of the tumor or when surgery is only partially successful or unsuccessful in achieving treatment goals. Approximately 50% of patients with acromegaly prove to be candidates for pharmacological treatment. Somatostatin, secreted by neuroendocrine cells of the hypothalamus, inhibits GH release from both the normal pituitary and pituitary adenomas by stimulating somatostatin receptors. Therefore, somatostatin receptor agonists can be effective in reducing serum GH and IGF-1 levels. Somatostatin analogs are usually the initial pharmacologic treatment employed; however, these drugs have limitations because they are injectables and result in an incomplete response in approximately 50% of patients. Additional pharmacological treatment options include dopamine agonists or GH receptor antagonists, which may be used in combination with somatostatin agonists.

Paltusotine has received Orphan Drug Designation in the United States by the Food and Drug Administration for the treatment of acromegaly (DRU-2017-5766).

Protocols for the treatment of acromegaly with paltusotine are disclosed in U.S. Patent Application Publication No. 2022/0387420, the entire contents of which is incorporated by reference.

Neuroendocrine Tumors (NETs) and Carcinoid Syndrome

Neuroendocrine tumors (NETs) arise from cells of the enteroendocrine system in the gastrointestinal (GI) tract (approximately 70% of cases), the lung (approximately 25% of cases), and more rarely, the pancreas. The estimated 20-year limited-duration prevalence of NETs in the United States as of 1 Jan. 2014 was 171,321. Approximately 48% of these tumors are locally advanced or metastatic at the time of diagnosis.

NETs may present clinically with symptoms of tumor growth (abdominal pain and occasionally bowel obstruction) or may be detected incidentally during imaging or endoscopic procedures performed for unrelated reasons. Approximately 10% to 20% of these tumors may present with symptoms that include flushing and diarrhea, referred to as carcinoid syndrome. Carcinoid syndrome is caused by secretion of serotonin and other vasoactive substances by the tumor directly into the systemic circulation, usually from hepatic metastases of mid-gut NETs.

Excess serotonin and other hormonally active products (including histamine, tachykinins, kallikrein, and prostaglandins) produced by some NETs are responsible for the symptoms collectively referred to as carcinoid syndrome. These symptoms most commonly include cutaneous flushing (seen in 85%) and recurrent watery diarrhea and cramping (seen in 75%-85%). Bronchospasm, venous telangiectasia, right-sided cardiac valvular lesions, and mesenteric and retroperitoneal fibrosis can also be present. Serotonin is a key contributor to the diarrhea and mesenteric, retroperitoneal, and cardiac fibrosis seen in this disease, but it does not cause cutaneous flushing.

Carcinoid syndrome is most common in patients when NETs that have originated in the distal small intestine or proximal colon (mid-gut) have metastasized to the liver. It is thought that excess serotonin secreted by hepatic metastases bypass first-pass hepatic inactivation, reaching the circulation directly and mediate the symptoms. Rarely, lung or ovarian NETs can release hormones directly into the systemic circulation and produce symptoms without metastases. Carcinoid syndrome associated with bronchial NETs is often atypical, exhibiting episodes of flushing and/or diaphoresis that may be accompanied by additional symptoms such as tremor, periorbital edema, lacrimation, salivation, and edema.

Since carcinoid syndrome usually occurs from intestinal NETs with liver metastases, surgical intervention is often very difficult for most patients. Hepatic resection or ablation can benefit patients in whom at least 90% of disease bulk can be eliminated. Treatment with somatostatin receptor ligand therapies octreotide or lanreotide have been shown to improve symptoms of carcinoid syndrome and to slow the growth of the underlying NET.

For those with persistent symptoms on somatostatin receptor ligand therapies, options include local therapy for liver metastases, adjunctive therapy with telotristat, interferon-alpha, antidiarrheals, everolimus, or peptide receptor radioligand therapy (PPRT).

Daily oral treatment with paltusotine may achieve higher drug concentrations in the liver, which is the most common source of the vasoactive mediators causing carcinoid syndrome symptoms. Therefore, paltusotine has the potential to improve treatment outcomes by achieving symptom control while eliminating painful injections.

Paltusotine Formulations

Capsules: Paltusotine is available as 10 mg (Swedish Orange Size 2) solid dose capsules. The dose strength is expressed as free base equivalent of paltusotine. The pharmaceutically acceptable excipients used for the preparation of the capsule formulation include mannitol, microcrystalline cellulose, croscarmellose sodium, vitamin E polyethylene glycol succinate, colloidal silicon dioxide, sodium stearyl fumarate, and Swedish Orange opaque capsule (red iron oxide, titanium dioxide, and gelatin). The excipients are common for solid oral formulations and are considered generally regarded as safe (GRAS) in the US and EU and are below the maximum allowable limits provided in the FDA's Inactive Ingredient Database (IID).

Tablets: Paltusotine is available as immediate release tablets containing an amorphous spray-dried dispersion of paltusotine in a water-soluble polymer, copovidone. The tablets are coated with a water-soluble, pink colored film. The drug product is supplied as a single strength of 20 mg tablets. The dose strength is expressed as free base equivalent of paltusotine. The excipients used in the manufacture of the paltusotine tablet include copovidone (for the spray-dried dispersion), mannitol, microcrystalline cellulose, crospovidone, colloidal silicon dioxide, magnesium stearate, and Opadry pink coating (hypromellose, titanium dioxide, triacetin, iron oxide-yellow, and iron oxide-red). The excipients are common for solid oral formulations and are considered GRAS in the US and EU and are below the maximum allowable limits provided in the FDA's IID. Paltusotine 20 mg tablets are packaged in 36-count high-density polyethylene (HDPE) bottles with desiccant, capped with child-resistant closures, and sealed with heat-induction seal. Paltusotine tablets are stored at 15 to 30° C. conditions.

Paltusotine formulations, including those described above, are disclosed in U.S. Pat. No. 11,266,641, the entire contents of which is incorporated by reference.

EXAMPLES

Example 1: A Phase 1, Open-Label, Single-Dose Study to Assess the Mass Balance, Route of Elimination, and Metabolic Profile of [$^{14}$C]-Labeled Paltusotine in Healthy Male Volunteers (ADME Study)

This was a Phase I, open-label, single-dose study with a primary objective to characterize the absorption, distribution, metabolism, excretion, and mass balance of a single oral dose of 20 mg paltusotine containing 3.0 MBq (80 µCi) of [$^{14}$C]-labeled paltusotine in healthy male subjects.

The use of radiolabeled molecules (usually [$^{14}$C]) is a common method used to ascertain information on the elimination routes and metabolic fate of a compound at an early stage of development. This evaluation will provide an estimate of basic PK parameters, an assessment of the routes and rates of elimination of radioactivity, and identification of metabolites and metabolic pathways. These data can be compared with similar data obtained from nonclinical studies, both from a PK and metabolic point of view.

Dose Selection

A dose of 20 mg paltusotine was chosen for the oral dose in the ADME study as a possible therapeutic dose estimated by PD activities of suppression of growth hormone releasing hormone (GHRH) stimulated GH secretion. The AUC for paltusotine increased dose-dependently within the dose range of 1.25 to 20 mg (SAD) and 5 to 30 mg (multiple ascending dose [MAD]) after oral administration in healthy adult male subjects.

The dose of [$^{14}$C] (approximately 3.0 MBq) to be administered was chosen to ensure successful profiling (and identification) of metabolites.

Patient Population

A sample size of 6 male subjects is a commonly accepted number of subjects for ADME studies and is considered sufficient to achieve the study objectives.

Study Design

Subjects received a single oral dose of 20 mg paltusotine as an oral solution containing 3.0 MBq (80 µCi) of radioactivity on Day 1. For oral dosing, the total volume ingested by the subject, including the study drug (10 mL), the rinse solutions (a total of 100 mL; 2 drug vial rinses with 50 mL of water per rinse), and tap water (130 mL), was 240 mL. The subjects had to ingest all solutions in the upright position within 2 minutes between 8 AM and 11 AM after an overnight fast of at least 10 hours. Fasting continued for a period of 4 hours after oral drug administration. The time of oral dosing administration was recorded, and the empty study drug vials were measured for residual radioactivity.

Subjects were discharged on Day 8 (approximately 168 hours after drug administration) if at least 90% of the administered radioactivity was recovered in the urine and feces since dosing (Day 1), and the total radioactivity in urine and feces was less than or equal to 1% of the total administered dose over a 24-hour period on 2 consecutive pharmacokinetic (PK) sample collection days, as determined by quick counts, a rapid method to measure radioactivity in urine and feces. If the criteria for discharge were not met on Day 8, subjects were required to remain confined for a maximum of 13 additional days (Days 9 to 21) until the criteria were met (daily check by quick counts). If the criteria for discharge were still not met on Day 21, subjects were discharged and requested to continue the collection of urine and feces at home and bring these specimens to the clinical research center every 2 to 3 days until Day 28, or until the discharge criteria were met, whichever came first.

Blood Sampling

Blood samples were taken for the analysis of unlabeled paltusotine and [$^{14}$C]-paltusotine concentrations, and metabolite profiling. Blood samples for analysis of pharmacokinetic parameters of paltusotine in plasma, quantification of total radioactivity in blood and plasma, and metabolite profiling were collected at predose and 0.25, 0.5, 0.75, 1, 1.5, 2, 3, 4, 8, 12, 24, 48, 72, 120, and 168 hours postdose (and every 48 hours thereafter, if needed, to assess radioactivity).

Urine Collection

Urine was collected for the analysis of total radioactivity, for quick counts of total radioactivity, and for metabolite profiling. The subjects were instructed to urinate completely before study drug administration and at the end of each collection interval. A baseline urine sample was collected within 12 hours prior to each study drug administration. Urine was collected for quantification of total radioactivity and metabolite profiling at predose, 3 intervals on Day 1 (at 0-4, 4-8, and 8-24 hours postdose), and every 24 hours thereafter until discharge criteria were met.

Feces Collection

All fecal excretions were collected for the analysis of total radioactivity, for quick counts of total radioactivity, and for metabolite profiling. A baseline fecal sample was collected within 48 hours prior to study drug administration and could be collected at home. The baseline sample was taken from the last bowel movement before study drug intake. Feces were collected for quantification of total radioactivity and metabolite profiling at predose and in 24-hour intervals until discharge criteria were met.

Analytics

Analysis of paltusotine in plasma was performed by Q2 Solutions (IQVIA, Itaca, NY, USA) using a validated liquid chromatography-tandem mass spectrometry (LC-MS/MS) method. The lower limit of quantitation (LLOQ) for paltusotine in plasma was 0.5 ng/mL.

Analysis of total $^{14}C$ radioactivity in plasma, whole blood, urine, and feces was performed at the bioanalytic laboratory of PRA Heath Sciences via a validated liquid scintillation counting method. The LLOQ for total reactivity was 3.36 ng-eq/mL in plasma and 5.6 ng-eq/mL in whole blood.

Metabolite profiling of plasma, urine, and feces was performed at WuXi AppTec (Cranbury, NJ, USA). For plasma, samples were pooled by timepoint (0.5, 1, 1.5, 2, 4, 8, 12, and 24 hours postdose) for metabolite profiling. In addition, plasma samples were pooled by participant across timepoints (0-48 hours) using the Hamilton method and analyzed to determine the quantitative profile of radiolabeled components. Prior to radio-profiling, plasma samples were extracted using solid phase extraction.

For urine and feces, samples were pooled by timepoint (0-8, 8-24, and 24-72 hours postdose). Prior to radio-profiling, urine samples were centrifuged to remove solids, and fecal homogenates were extracted with acetonitrile. Plasma and fecal extracts and urine supernatants were subjected to LC separation and fraction collection. Metabolite characterization was performed using LC-MS/MS in conjunction with an appropriate radioactivity monitor. Metabolite structure was characterized through interpretation of mass spectral fragmentation patterns and comparisons with reference standards, if available.

CONCLUSIONS

Following single oral administration of 20 mg (80 µCi) of [$^{14}C$]-paltusotine to healthy male volunteers, the only drug-related component detected in human plasma (0-48 h) was paltusotine. The absence of detectable metabolites in human plasma suggests that measurement of paltusotine alone is sufficient to characterize PK and PD of paltusotine.

Following a single oral dose of 20 mg (80 µCi) [$^{14}C$]-paltusotine to healthy male volunteers, the total mean recovery of administered radioactivity was 94%, with 90% recovered in the feces and 3.9% recovered in the urine. This suggested that the primary route of excretion was feces. Most of the total radioactivity (88% of the administered dose) was excreted over 120 h.

Metabolic profiling of excreta determined that approximately 84% of the dose was excreted in the feces in humans, of which unchanged paltusotine was the most abundant component accounting for 39.7%. M632/1 was the major metabolite accounting for 20.4% of the dose and M676/1, M472/1 and M648/1 accounted for 2.53%, 7.92% and 4.26% of the dose, respectively (See FIG. 1). The extent of excretion of unchanged paltusotine or its metabolites in human bile is not known. Metabolites found in feces were likely secreted into the bile.

The amount of unchanged paltusotine and metabolites excreted in the urine of humans after a single oral dose of radiolabeled paltusotine was low, representing <4% of the total administered radioactivity. In human urine, M632/1 and paltusotine were the two major components accounting for 1.44% and 1.33% of dose, respectively, whereas the other metabolites M472/1, M648/1, and M676/1 were minor components accounting for 0.15% to 0.2% of the dose.

Figure 2:
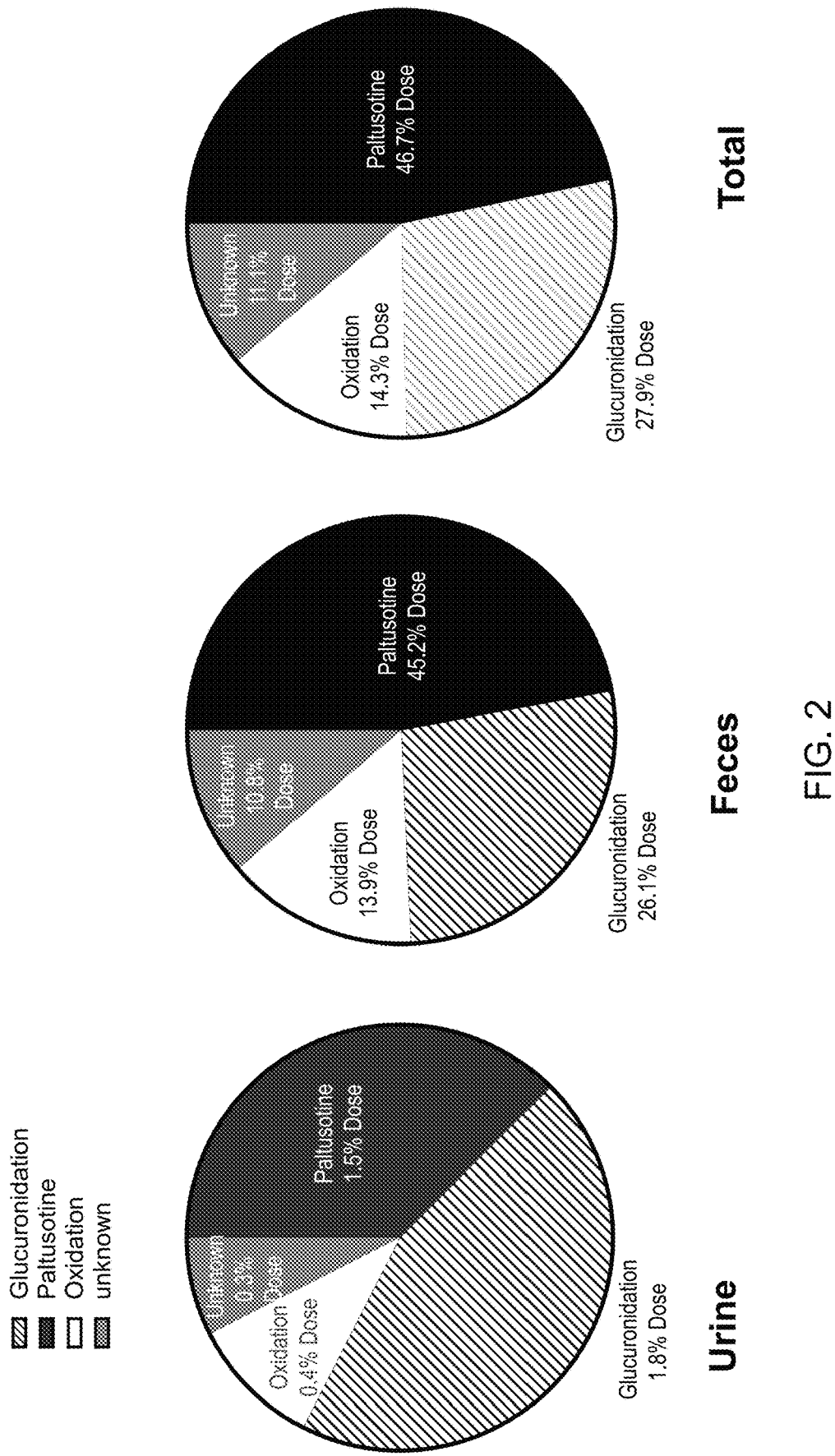
FIG. 2 depicts a summary of % recovery of paltusotine and excretory metabolites in humans following oral administration of a single dose of [$^{14}$C]paltusotine.
Figure 3A:
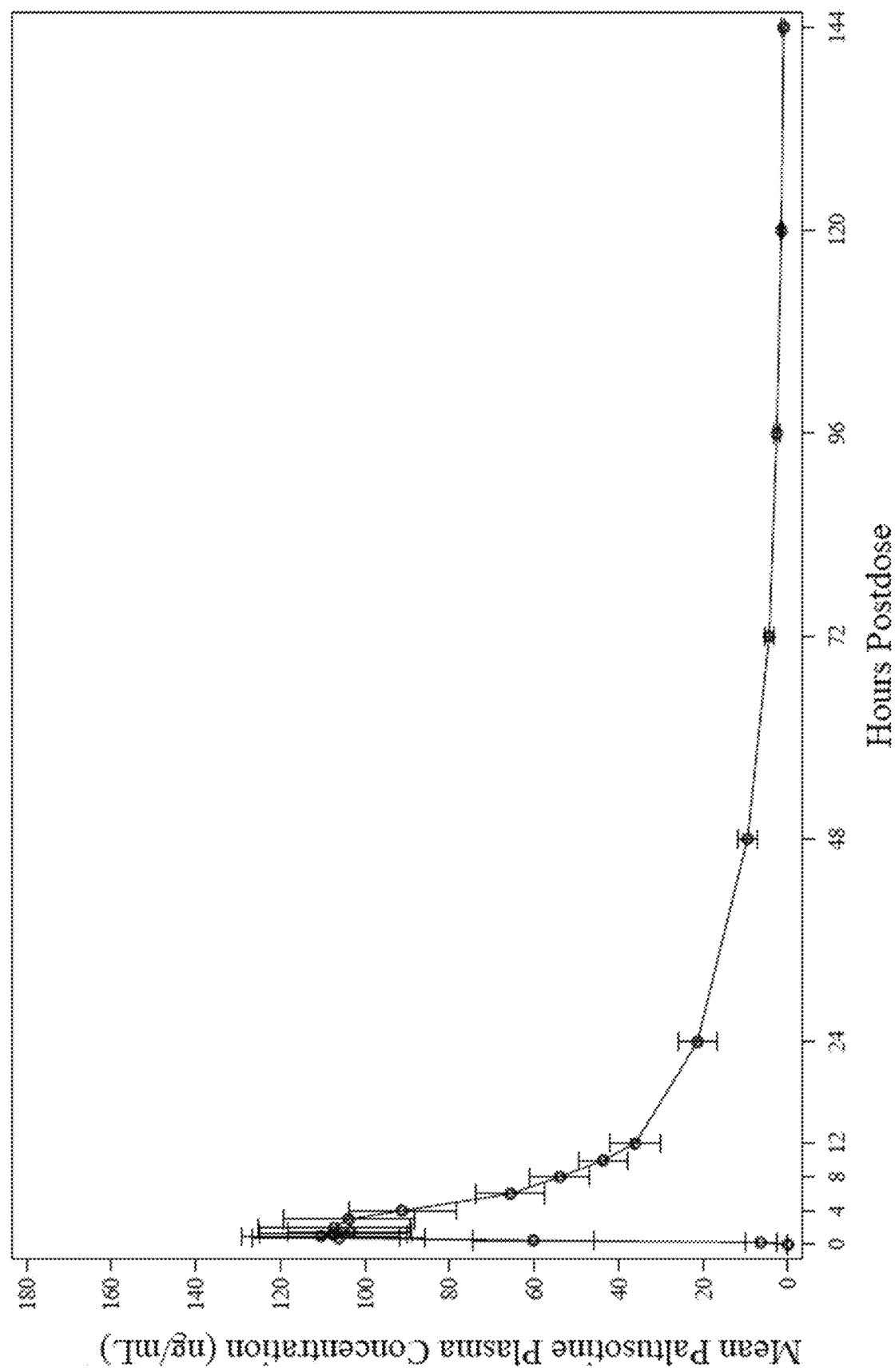
FIG. 3A-FIG. 3D depict the mean plasma concentrations of paltusotine versus time of patients.
Figure 3B:
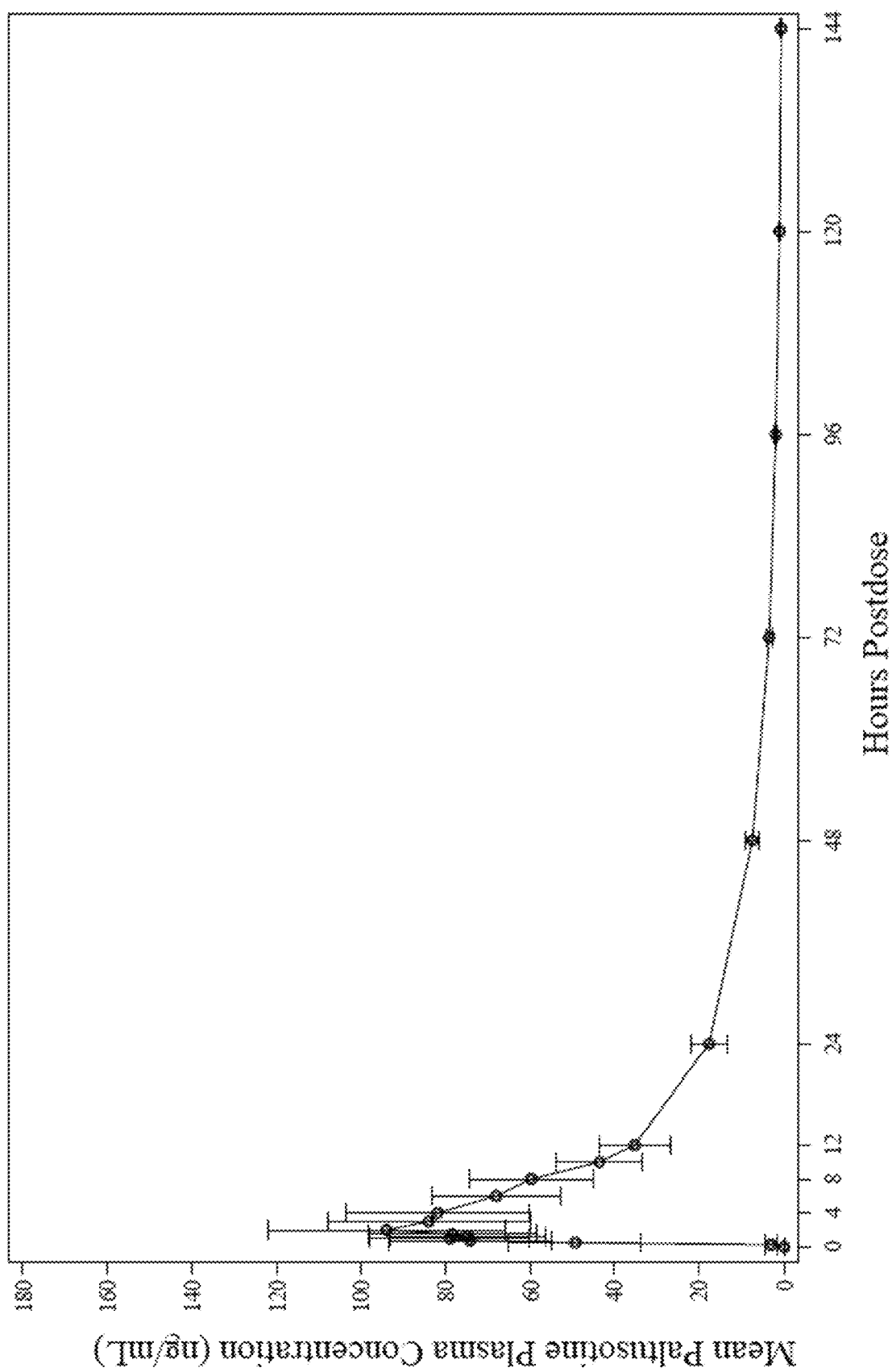
Figure 3C:
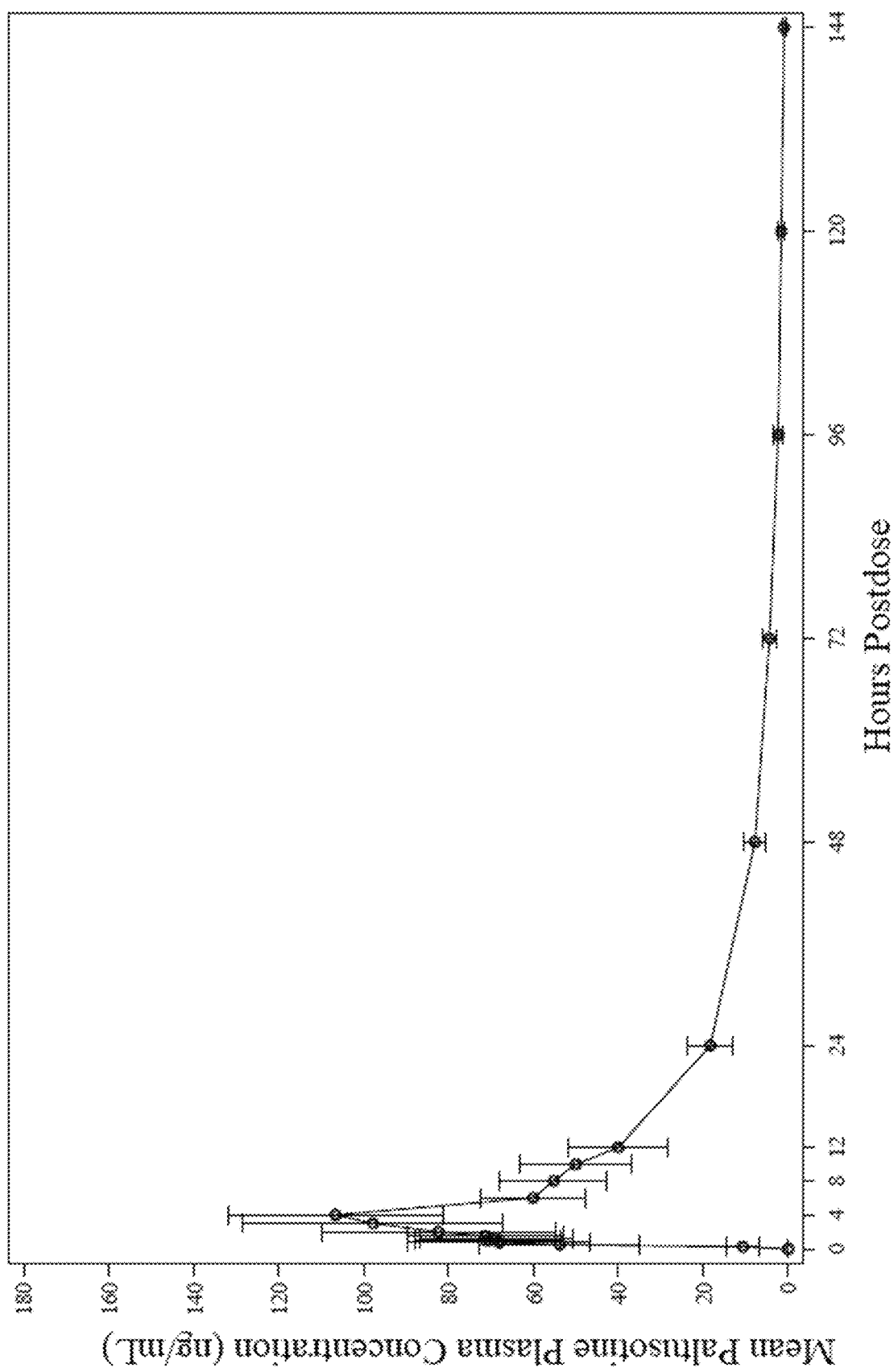
Figure 3D:
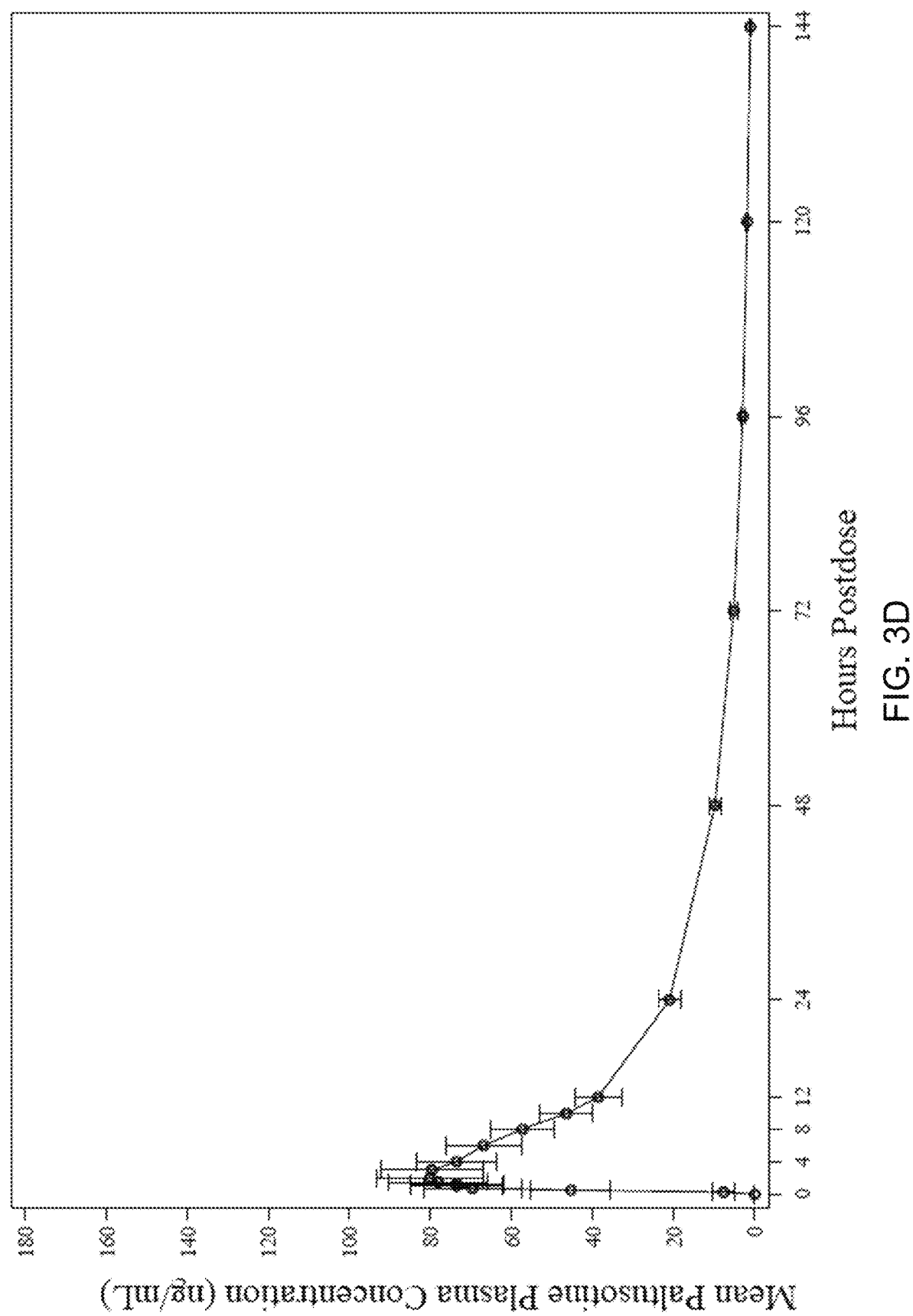

In vitro and in vivo studies of paltusotine in humans suggests that CYP-mediated oxidation and uridine glucuronosyl transferase (UGT)-mediated glucuronidation are the primary pathways involved in metabolic clearance of paltusotine (see FIG. 1). Scaling of paltusotine and the excretory metabolites to estimate the overall metabolic clearance routes in humans after [$^{14}C$]paltusotine administration to humans suggests that glucuronidation is the major metabolic pathway accounting for 27.9% of the dose and that the oxidative route accounts for a total of 14.3% (See FIG. 2). This is consistent with the in vitro studies, which suggest that the contribution of CYP-mediated metabolism is ~16.8%.

CYP phenotyping studies using human liver microsomes and recombinant CYP450s indicate that CYP3A4/5 catalyzes the oxidative metabolism of paltusotine with minor contribution of CYP2D6, whereas studies of paltusotine with recombinant uridine diphosphate glucuronosyltransferase (UGT) with and without 2% BSA suggest that formation of M632/1 is catalyzed by UGT1A1, UGT1A3, UGT1A8, UGT1A9 and UGT1A10.

Since paltusotine is metabolized in the human liver, patients with hepatic impairment would be expected to demonstrate increased PK exposures of paltusotine compared to patients with normal liver function who are on the same therapeutic dosage. Therefore, it is expected that it will be necessary to assess hepatic function prior to or during treatment in order to reduce risk and ensure patient safety. To reduce risk and ensure safety it is expected that paltusotine dose modification will be necessary for patients with hepatic impairment relative to patients with normal liver function.

Example 2: A Phase 1, Open-Label, Single-Dose Study to Evaluate the Safety, Tolerability, and Pharmacokinetics of Paltusotine in Subjects with Varying Degrees of Hepatic Impairment This was a Phase I, multicenter, open-label, single-dose study with a primary objective to compare the PK profile of a single dose of paltusotine in subjects with varying degrees of hepatic impairment with that of healthy matched control subjects.

The secondary objective of the study was to assess the safety and tolerability of a single dose of paltusotine in subjects with varying degrees of hepatic impairment.

Dose Selection

Dose and exposure response analyses of paltusotine Phase 2 studies in patients with acromegaly identified a 40 to 60 mg dosage range of oral paltusotine is expected to result in IGF-1 suppression similar to that of injected long-acting somatostatin receptor ligands. A 20 mg dose was available for patients in Phase 3 studies who were unable to tolerate higher doses. The 20 mg dose was used for this study due to expected increases in the PK exposures of paltusotine in subjects with hepatic impairment.

Immediate-release paltusotine tablets were administered to patients containing 20 mg of paltusotine in a spray-dried dispersion, and the following inactive excipients: copovidone (for the spray-dried dispersion), mannitol, microcrystalline cellulose, crospovidone, colloidal silicon dioxide, magnesium stearate, and Opadry pink coating (hypromellose, titanium dioxide, triacetin, iron oxide yellow, and iron oxide red).

The single oral dose of 20 mg of paltusotine administered in this study was evaluated per recommendations provided in the US FDA "Guidance for Industry, Pharmacokinetics in Patients with Impaired Hepatic Function: Study Design, Data Analysis, and Impact on Dosing and Labeling."

Patient Population

Overall, 36 male and female subjects were enrolled, including 14 subjects with normal hepatic function, 8 subjects with mild stable hepatic impairment (Group 1), 8 subjects with moderate stable hepatic impairment (Group 2), and 6 subjects with severe stable hepatic impairment (Group 3). Healthy subjects with normal hepatic function (Group 4) were matched with hepatically impaired subjects according to sex, age (±10 years), and BMI (±20%). A reasonable attempt was made to match healthy subjects with hepatically impaired subjects in terms of race. Healthy subjects may have matched to more than 1 subject in different hepatic impairment groups but not more than 1 subject within each hepatic impairment group. Healthy subjects were recruited into the study after a sufficient number of hepatically impaired subjects were enrolled in Groups 1, 2, and 3.

A total of 36 subjects were enrolled in the study, and all subjects completed the study. All 36 enrolled subjects (100.0%) were included in the safety and PK analysis populations.

Method of Assigning Patients to Treatment Groups

The Child-Pugh scale was used to categorize the degree of hepatic impairment for assignment into the mild (score of 5-6), moderate (score of 7-9), and severe hepatic impairment (score of 10-15) groups.

Study Design

A written informed consent in compliance with US Title 21 CFR Part 50 was obtained from each subject before entering the study and before any study related procedure that involved risk to the subject was performed. The subject received a signed, dated copy of the informed consent form.

The study included a screening period (Days −28 to −2), check-in (Day −1), and a treatment period (Days 1 to 7). On Day 1, all subjects received a single oral dose of 20 mg of paltusotine (1×20 mg tablet) administered with 240 mL of room temperature water following an overnight fast (nothing to eat or drink except water) of at least 10 hours. Subjects remained fasted and upright (seated or standing) for 4 hours after dosing. Water was permitted as desired except for the period 1 hour before and 1 hour after administration of study drug. Subjects received standardized meals that were scheduled at the same time daily during the study.

Subjects underwent end of study procedures and were discharged from the clinical site on Day 7. The duration of the study, excluding screening, was approximately 8 days.

Drug Concentration Measurements

Serial blood samples for PK analysis of paltusotine were collected before dosing (0 hour) and up to 144 hours after administration of paltusotine.

Blood samples for analysis of paltusotine concentrations in plasma were collected at the following time points: before dosing (0 hour) and at 0.25, 0.5, 0.75, 1, 1.25, 1.5, 2, 3, 4, 6, 8, 10, 12, 24, 48, 72, 96, 120, and 144 hours after administration of paltusotine.

Collection windows for blood samples were as follows: ±5 minutes for blood samples collected up to the 1-hour time point; ±15 minutes for blood samples collected up to the 12-hour time point; ±1 hour for blood samples collected at the 24-hour time point; ±4 hours for blood samples collected after the 24-hour time point.

Pharmacokinetic samples were analyzed using a validated liquid chromatography coupled with tandem mass spectrometry assay for paltusotine in human plasma.

Plasma concentration-time data was analyzed by non-compartmental analysis using Phoenix® WinNonlin® Version 8.3 (Certara USA, Inc., Princeton, NJ).

The PK assessments used in this study are the accepted standard to describe the PK profile of a drug in plasma. The safety assessments performed were standard and are recognized as reliable, accurate, and relevant.

Adverse Events (AEs)

The investigator was responsible for reporting all AEs observed or reported during the study from the time the subject signs the informed consent form (ICF) until end of study (EOS), regardless of the relationship to study drug or clinical significance. Any serious adverse event (SAE) occurring after the ICF was signed and up until 4 weeks after the last paltusotine dose was to be reported. If there was any doubt as to whether a clinical observation was an AE, the event was to be reported.

Clinical Laboratory Assessments

Blood and urine samples for hematology, serum chemistry, urinalysis, and screening tests were collected at screening, check-in (Day −1), Day 3, and end of study.

The following clinical laboratory assessments were performed:

Hematology: Absolute neutrophil count and differential, hematocrit, hemoglobin, mean corpuscular hemoglobin, mean corpuscular hemoglobin concentration, leukocytes (basophils, eosinophils, lymphocytes, monocytes, neutrophils), mean corpuscular volume, platelet count, red blood cell count, and red blood cell distribution width.

Coagulation: Activated partial thromboplastin time and/or partial thromboplastin time, international normalized ratio, and prothrombin time.

Serum Chemistry: Alanine aminotransferase, albumin, alkaline phosphatase, amylase, aspartate aminotransferase, bilirubin (total), blood urea nitrogen, calcium, carbon dioxide, chloride, cholesterol (total, high-density lipoprotein, and calculated low-density lipoprotein), creatinine, gamma-glutamyltransferase, globulin, glucose, lactate dehydrogenase, lipase, phosphorus, potassium, sodium, total protein, triglycerides, and uric acid.

Urinalysis: Appearance, bilirubin, color, glucose, ketones, leukocytes, reflex microscopy (performed if dipstick was positive for protein or the blood value is 1+ or greater; and included bacteria, casts, crystals, epithelial cells, red blood cells, and white blood cells), nitrites, occult blood, pH, protein, specific gravity, and urobilinogen.

Serology: Hepatitis B surface antigen, hepatitis C virus antibody, and HIV antibody types 1 and 2 (screening only).

Other Analyses (All subjects): Urine drug screen (amphetamines, barbiturates, benzodiazepines, cannabinoids, cocaine metabolites, methamphetamines, methylenedioxymethamphetamine, and opiates [including heroin, codeine, and oxycodone]), and alcohol breath test (screening and check in).

Other Analyses (female subjects): Follicle-stimulating hormone (performed at screening to confirm postmenopausal status), serum human chorionic gonadotropin pregnancy test (screening only), and urine human chorionic gonadotropin pregnancy test (check-in and end of study).

Vital Sign Measurements

Vital signs were measured at screening; check-in; within 1.5 hours prior to paltusotine dosing; 4, 8, and 12 hours following administration of paltusotine; Days 2 through 6 (in the morning); and end of study, after the subject had been in the seated position for at least 5 minutes. Post-dose vital sign measurements were taken ±15 minutes from the nominal post-dose time points.

Vital signs included systolic and diastolic blood pressure, pulse rate, respiratory rate, and oral (or equivalent) body temperature.

Physical Examination

Subjects underwent physical examination at the time points specified in the schedule of events. A full physical examination included, at minimum, assessment of skin, head, ears, eyes, nose, throat, neck, thyroid, lungs, heart, cardiovascular, abdomen, lymph nodes, and musculoskeletal system/extremities. A brief physical examination included, at minimum, assessment of skin, lungs, cardiovascular system, and abdomen (liver and spleen). Interim physical examinations were performed at the discretion of the investigator, if necessary, to evaluate adverse events or clinical laboratory abnormalities.

Twelve-Lead Electrocardiogram

Triplicate 12-lead ECGs (approximately 1 minute apart) were obtained at screening, check-in (Day −1), 2 (±1) hours following administration of paltusotine, and end of study, after the subject had been in the supine position for at least 10 minutes.

Electrocardiogram assessments included comments on whether the tracings were normal or abnormal, rhythm, presence of arrhythmia or conduction defects, morphology, any evidence of myocardial infarction, or ST-segment, T-Wave, and U Wave abnormalities. In addition, measurements of the following intervals were measured and reported: RR interval, PR interval, QRS width, QT interval, and QTcF.

Genetics

On Day 1, a blood sample was collected for genotyping for the determination of the UGT1A1 genotype.

Subjects whose UGT1A1 genotype classification was "poor metabolizer" (PM) were presented also for PM versus non-PM classified subjects as PM could not be determined by direct comparison of different groups.

Pharmacokinetic Parameters and Analysis

The following pharmacokinetic parameters were calculated:

Area under the plasma concentration versus time curve from time 0 to the last quantifiable concentration ($AUC_{0-t}$);

Area under the plasma concentration versus time curve from time 0 to 24 hours ($AUC_{0-24}$);

Area under the plasma concentration versus time curve from time 0 extrapolated to infinity ($AUC_{0-\infty}$);

Maximum observed plasma concentration ($C_{max}$);

Time to maximum observed plasma concentration ($T_{max}$);

Delay time between time of dosing and time of appearance of measurable test article ($T_{lag}$);

Apparent terminal phase half-life ($t_{1/2}$);

Apparent terminal rate constant ($\lambda_z$);

Apparent mean residence time (MRT);

Apparent total body clearance (CL/F); and

Apparent volume of distribution ($V_z/F$).

Plasma PK parameters of paltusotine are summarized in Table 1 below:

TABLE 1

| Summary of Plasma PK Parameters (PK Population) | | | | |
|---|---|---|---|---|
| | Mild | Moderate | Severe | Normal |
| Parameter | Mean ± SD (8) | Mean ± SD (8) | Mean ± SD (6) | Mean ± SD (14) |
| $AUC_{(0-t)}$ (ng × h/mL) | 1821.45 ± 888.264 | 1575.88 ± 1043.913 | 1682.69 ± 1185.041 | 1776.04 ± 913.900 |
| $AUC_{(0-24)}$ (ng × h/mL) | 1152.53 ± 467.219 | 1054.26 ± 728.951 | 1095.09 ± 704.295 | 1068.75 ± 544.746 |
| $AUC_{(0-inf)}$ (ng × h/mL) | 1884.54 ± 925.982 | 1616.80 ± 1046.068 | 1736.59 ± 1225.891 | 1838.18 ± 946.732 |
| $C_{max}$ (ng/mL) | 133.28 ± 56.637 | 100.21 ± 74.583 | 110.33 ± 72.684 | 101.35 ± 53.720 |
| $t_{max}$ (h)[a] | 1.63 (0.8, 4.0) | 2.00 (0.8, 6.0) | 3.00 (0.8, 4.0) | 2.00 (0.8, 6.0) |
| $t_{lag}$ (h)[a] | 0.00 (0.0, 0.3) | 0.13 (0.0, 0.5) | 0.00 (0.0, 0.3) | 0.00 (0.0, 0.3) |
| $t_{1/2}$ (h) | 29.54 ± 9.405 | 31.24 ± 7.935 | 29.45 ± 8.382 | 32.75 ± 6.917 |
| $MRT_{(0-inf)}$ (h)[a] | 28.31 (19.1, 38.0) | 25.19 (22.8, 50.7) | 29.23 (15.2, 39.8) | 34.60 (20.7, 46.6) |
| CL/F (L/h) | 15.50 ± 13.496 | 24.89 ± 25.914 | 15.92 ± 8.507 | 14.05 ± 7.521 |
| $V_z/F$ (L) | 565.18 ± 347.507 | 1052.01 ± 1105.764 | 666.01 ± 479.113 | 660.49 ± 407.317 |
| | Geometric Mean Ratio[b] (90% CI) | Geometric Mean Ratio[b] (90% CI) | Geometric Mean Ratio[b] (90% CI) | |
| $AUC_{(0-t)}$ (ng × h/mL) | 1.00 (0.596, 1.679) | 0.74 (0.441, 1.242) | 0.90 (0.510, 1.594) | |
| $AUC_{(0-inf)}$ (ng × h/mL) | 1.00 (0.601, 1.660) | 0.75 (0.451, 1.244) | 0.90 (0.514, 1.571) | |
| $C_{max}$ (ng/mL) | 1.35 (0.789, 2.311) | 0.76 (0.447, 1.307) | 1.05 (0.583, 1.902) | |

Abbreviations: SD = standard deviation; CI = Confidence interval.

Note:

Geometric mean ratio and 90% CIs are from an analysis of variance (ANOVA) with hepatic condition (normal, mild, moderate, severe) as a fixed effect and log transformed PK parameter as the dependent variable.

[a]Median (min, max)

[b]Geometric mean ratio compared to Normal subjects.

Sensitivity analysis results investigating the potential imbalance across hepatic impairment groups in the distribution of the baseline covariates used in subject matching (age and BMI) are presented in Table 2 below:

TABLE 2

Sensitivity Analysis of Geometric Mean Ratio of PK Parameters (PK Population)

| Parameter | Mild<br>Geometric Mean<br>Ratio[a] (90% CI) | Moderate<br>Geometric Mean<br>Ratio[a] (90% CI) | Severe<br>Geometric Mean<br>Ratio[a] (90% CI) |
|---|---|---|---|
| $AUC_{(0-t)}$<br>(ng × h/mL) | 0.95 (0.591, 1.515) | 0.71 (0.403, 1.254) | 0.93 (0.512, 1.702) |
| $AUC_{(0-inf)}$<br>(ng × h/mL) | 0.94 (0.591, 1.504) | 0.72 (0.414, 1.251) | 0.94 (0.516, 1.702) |
| $C_{max}$<br>(ng/mL) | 1.38 (0.871, 2.200) | 0.74 (0.389, 1.412) | 1.04 (0.586, 1.854) |

Abbreviations: CI = Confidence interval.
Note:
Geometric mean ratio and 90% CIs are from a matched pairs mixed models for repeated measures (MMRM) model with hepatic condition (normal versus. mild, moderate, or severe), age and BMI as fixed effects and log transformed PK parameter as the dependent variable. Separate models were fit for each hepatic impairment group.
[a]Geometric mean ratio compared to Normal subjects.

Figure 4:
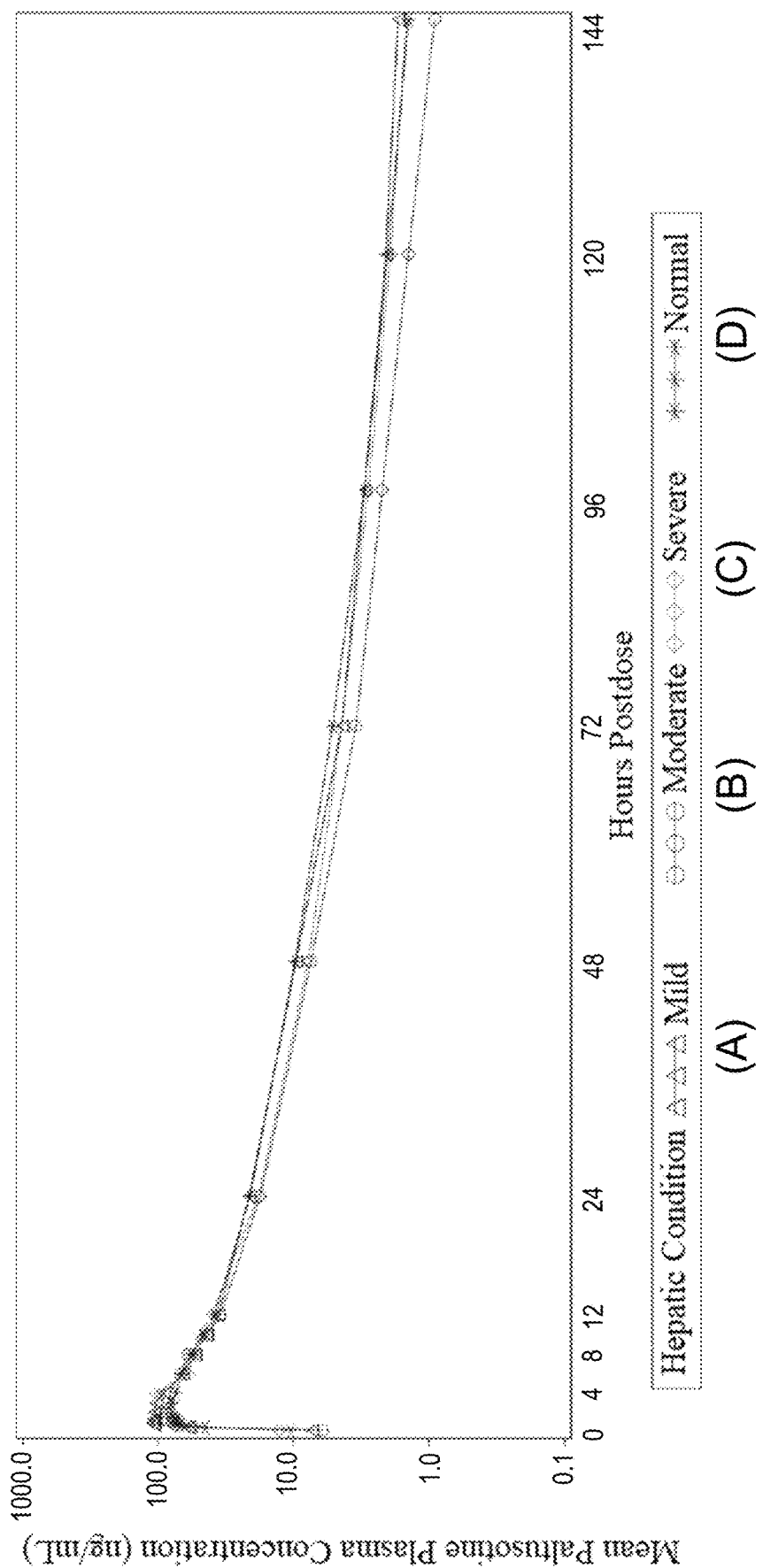
FIG. 4 depicts the mean plasma concentrations of paltusotine versus time semi-log of patients; (A) depicts the mean plasma concentration of paltusotine versus time semi-log of patients with mild hepatic impairment; (B) depicts the mean plasma concentration of paltusotine versus time semi-log of patients with moderate hepatic impairment; (C) depicts the mean plasma concentration of paltusotine versus time semi-log of patients with severe hepatic impairment; and (D) depicts the mean plasma concentration of paltusotine versus time semi-log of patients without hepatic impairment (i.e., normal patients).

As shown in FIG. 3 and FIG. 4, following a single oral administration of 20 mg paltusotine tablets to subjects with mild, moderate, or severe hepatic impairment, and normal hepatic function, mean plasma concentrations of paltusotine peaked rapidly and attained maximum concentration 1.6 hours to 3 hours postdose. Thereafter, plasma concentrations declined in a similar manner across all treatment groups and the concentration of paltusotine was measurable in systemic circulation through 144 hours postdose.

Figure 5:
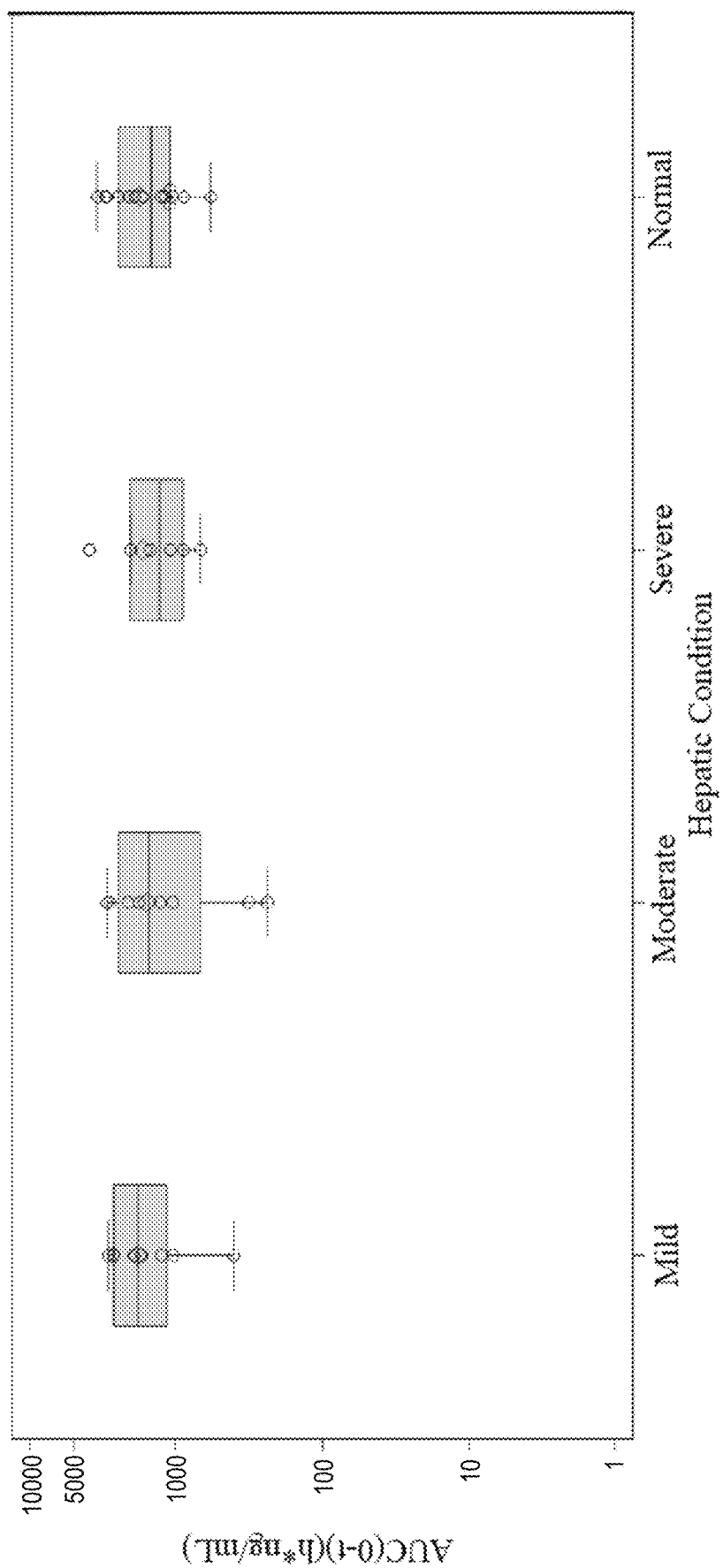
FIG. 5 depicts a boxplot of $AUC_{0-t}$ for each hepatic function group.
Figure 6:
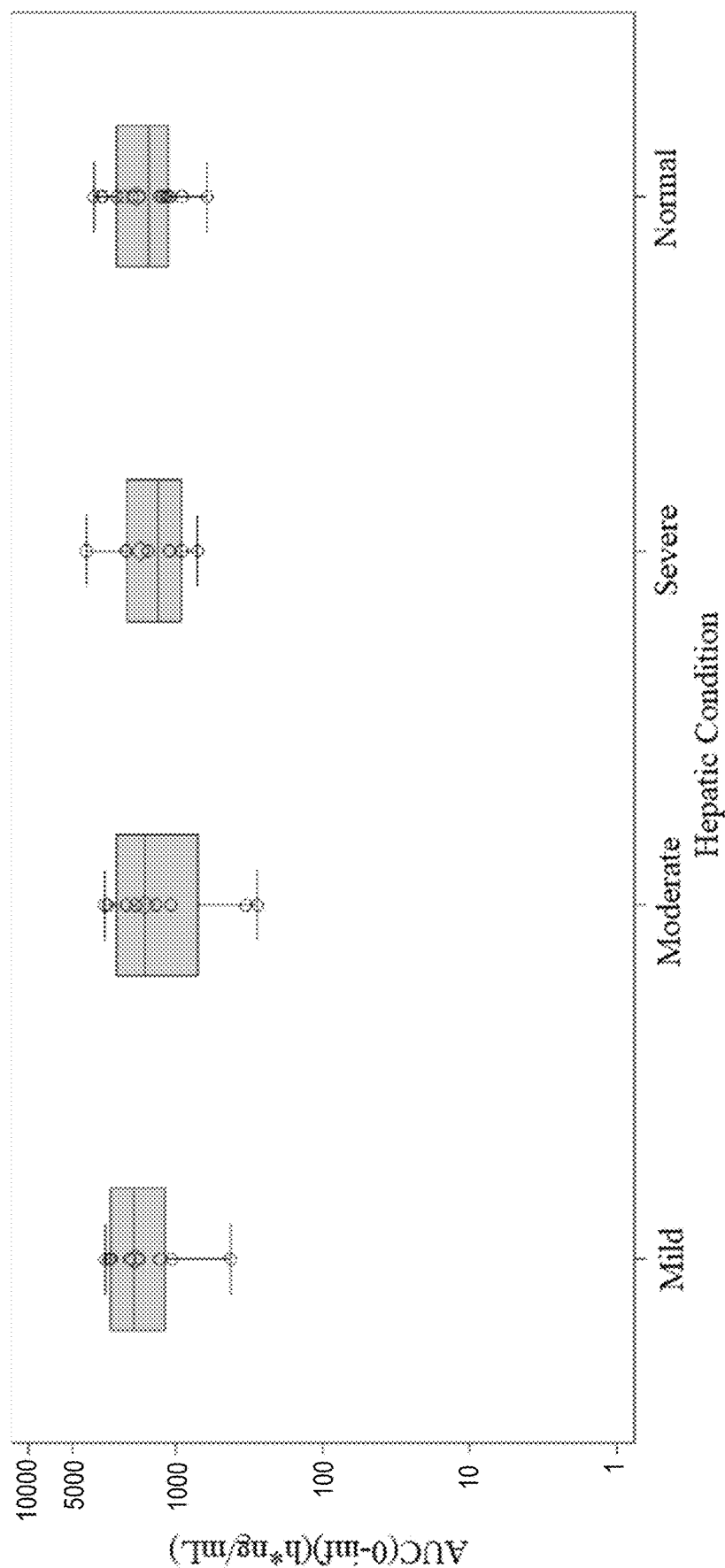
FIG. 6 depicts a boxplot of $AUC_{0-\infty}$ for each hepatic function group.
Figure 7:
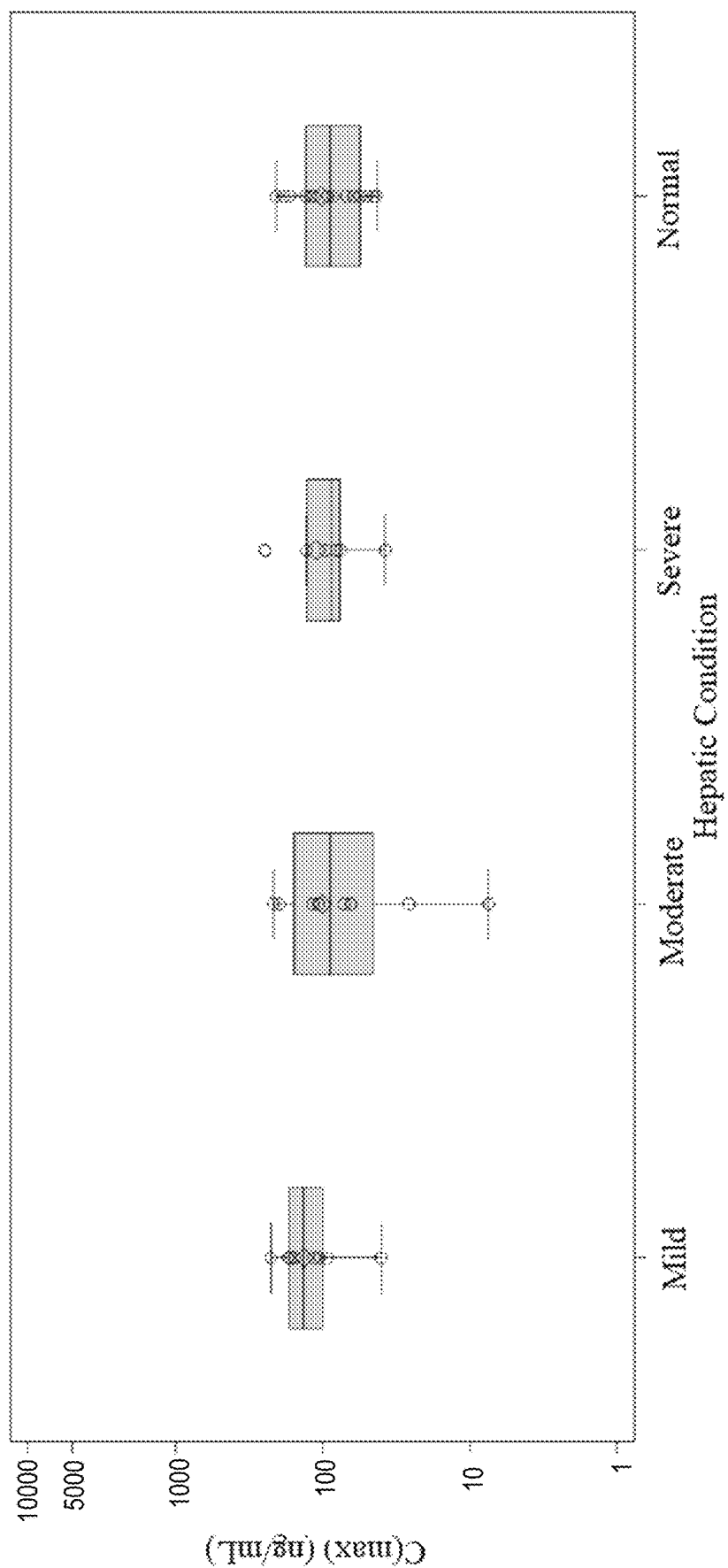
FIG. 7 depicts a boxplot of $C_{max}$ for each hepatic function group.

A boxplot of PK parameters for each hepatic function group is presented in FIGS. 5-7. Relative to the normal hepatic function group, the total plasma exposure (area under the plasma concentration versus time curve from time 0 to the last quantifiable concentration [$AUC_{0-t}$] and area under the plasma concentration versus time curve from time 0 extrapolated to infinity [$AUC_{0-inf}$]) of paltusotine was similar for subjects with mild and severe hepatic impairment with geometric mean ratios of 1.00 and 0.90 for mild and severe hepatic impairment groups, respectively. For subjects with moderate hepatic impairment, the $AUC_{0-t}$ and $AUC_{0-inf}$ of paltusotine was approximately 25% lower (0.74 and 0.75 geometric mean ratio [GMR]) relative to the normal hepatic function group. Overall, no trend was observed and the paltusotine total plasma exposure were considered similar across all hepatic function groups relative to the normal group.

Relative to the normal hepatic function group, the peak plasma exposure ($C_{max}$) of paltusotine was similar for subjects with severe hepatic impairment with GMR of 1.05. For subjects with mild hepatic impairment, $C_{max}$ of paltusotine was 35% higher (1.35 GMR) relative to the normal hepatic function group and for subjects with moderate hepatic impairment the $C_{max}$ of paltusotine was 24% lower (0.76 GMR). Overall, no trend was observed and the paltusotine peak plasma exposure may be considered similar across all hepatic function groups relative to the normal group.

The mean estimates for apparent terminal phase half-life ($t_{1/2}$) were similar across all groups. For mild and severe hepatic impairment groups, the mean apparent total body clearance after oral administration (CL/F) and apparent volume of distribution during terminal phase after oral administration ($V_z$/F) values were similar compared to the normal group, whereas the mean CL/F and $V_z$/F values were 1.8-fold and 1.6-fold higher for the moderate hepatic impairment group compared to the normal group; however, the variability in exposure parameters were generally highest in the moderate hepatic impairment group.

There did not appear to be an imbalance in the distribution of baseline covariates used in subject matching (age and BMI) as the GMRs were similar in both analyses.

Safety Evaluation

Safety and tolerability were assessed by the following endpoints: reported adverse events (AEs), clinical laboratory test results (hematology, coagulation, serum chemistry, and urinalysis), vital sign measurements, and 12-lead electrocardiogram results All 36 subjects who were enrolled in the study received all planned single doses of paltusotine 20 mg (1×20 mg tablet) and were included in the safety and PK analysis populations.

An overall summary of TEAEs is presented in Table 3. A summary of TEAEs by system organ class (SOC) and preferred term (PT) is presented in Table 4. A summary of TEAEs by PT is presented in Table 5. A summary of related TEAEs by PT is presented in Table 6.

TABLE 3

Overall Summary of Treatment-Emergent Adverse Events (Safety Population)

| | Mild<br>(N = 8) | Moderate<br>(N = 8) | Severe<br>(N = 6) | Normal<br>(N = 14) | Overall<br>(N = 36) |
|---|---|---|---|---|---|
| Total number of TEAEs reported | 3 | 4 | 4 | 6 | 17 |
| Subjects reporting any TEAE | 2 (25.0%) 3 | 2 (25.0%) 4 | 2 (33.3%) 4 | 4 (28.6%) 6 | 10 (27.8%) 17 |

TABLE 3-continued

Overall Summary of Treatment-Emergent Adverse Events (Safety Population)

| | Mild (N = 8) | Moderate (N = 8) | Severe (N = 6) | Normal (N = 14) | Overall (N = 36) |
|---|---|---|---|---|---|
| Subjects reporting TEAEs by maximum severity | | | | | |
| Severe | 1 (12.5%) 1 | 0 | 0 | 0 | 1 (2.8%) 1 |
| Moderate | 0 | 1 (12.5%) 1 | 1 (16.7%) 2 | 1 (7.1%) 1 | 3 (8.3%) 4 |
| Mild | 1 (12.5%) 2 | 1 (12.5%) 3 | 1 (16.7%) 2 | 3 (21.4%) 5 | 6 (16.7%) 12 |
| Subjects reporting TEAEs by strongest relationship group to study drug | | | | | |
| Related | 2 (25.0%) 2 | 2 (25.0%) 4 | 2 (33.3%) 2 | 3 (21.4%) 5 | 9 (25.0%) 13 |
| Not Related | 0 | 0 | 0 | 1 (7.1%) 1 | 1 (2.8%) 4 |
| Total number of SAEs reported | 1 | 0 | 0 | 0 | 1 |
| Subjects reporting any SAEs | 1 (12.5%) 1 | 0 | 0 | 0 | 1 (2.8%) 1 |
| Subjects reporting SAEs by strongest relationship group to study drug | | | | | |
| Related | 0 | 0 | 0 | 0 | 0 |
| Not related | 1 (12.5%) 1 | 0 | 0 | 0 | 1 (2.8%) 1 |

Notes:
Subjects were classified according to the highest severity if the subject reported >1 events; AEs with missing severity were considered severe for this summary. Subjects were classified according to the greatest relation if the subject reported >1 events; AEs with missing relation were considered related for this summary. Adverse events were summarized by number of subjects with AE (percentage) number of occurrences.
Abbreviations: SD = standard deviation; IQR = interquartile range; SAE = serious adverse event; TEAE = treatment-emergent adverse event.

TABLE 4

Treatment-Emergent Adverse Events by System Organ Class and Preferred Term (Safety Population)

| System Organ Class/ Preferred Term[a] | Mild (N = 8) | Moderate (N = 8) | Severe (N = 6) | Normal (N = 14) | Overall (N = 36) |
|---|---|---|---|---|---|
| Subjects reporting at least one TEAE | 2 (25.0%) 3 | 2 (25.0%) 4 | 2 (33.3%) 4 | 4 (28.6%) 6 | 10 (27.8%) 17 |
| Gastrointestinal disorders | 1 (12.5%) 1 | 1 (12.5%) 1 | 1 (16.7%) 1 | 4 (28.6%) 5 | 7 (19.4%) 8 |
| Diarrhea | 1 (12.5%) 1 | 1 (12.5%) 1 | 1 (16.7%) 1 | 3 (21.4%) 3 | 6 (16.7%) 6 |
| Abdominal discomfort | 0 | 0 | 0 | 1 (7.1%) 1 | 1 (2.8%) 1 |
| Epigastric discomfort | 0 | 0 | 0 | 1 (7.1%) 1 | 1 (2.8%) 1 |
| General disorders and administration site conditions | 1 (12.5%) 1 | 1 (12.5%) 2 | 0 | 0 | 2 (5.6%) 3 |
| Death | 1 (12.5%) 1 | 0 | 0 | 0 | 1 (2.8%) 1 |
| Fatigue | 0 | 1 (12.5%) 1 | 0 | 0 | 1 (2.8%) 1 |
| Pain | 0 | 1 (12.5%) 1 | 0 | 0 | 1 (2.8%) 1 |
| Nervous system disorders | 0 | 1 (12.5%) 1 | 1 (16.7%) 1 | 1 (7.1%) 1 | 3 (8.3%) 3 |
| Headache | 0 | 1 (12.5%) 1 | 1 (16.7%) 1 | 0 | 2 (5.6%) 2 |
| Paraesthesia | 0 | 0 | 0 | 1 (7.1%) 1 | 1 (2.8%) 1 |
| Blood and lymphatic system disorders | 0 | 0 | 1 (16.7%) 1 | 0 | 1 (2.8%) 1 |
| Neutropenia | 0 | 0 | 1 (16.7%) 1 | 0 | 1 (2.8%) 1 |
| Infections and infestations | 0 | 0 | 1 (16.7%) 1 | 0 | 1 (2.8%) 1 |
| COVID-19 | 0 | 0 | 1 (16.7%) 1 | 0 | 1 (2.8%) 1 |
| Renal and urinary disorders | 1 (12.5%) 1 | 0 | 0 | 0 | 1 (2.8%) 1 |
| Haematuria | 1 (12.5%) 1 | 0 | 0 | 0 | 1 (2.8%) 1 |

Notes:
At each level of summarization (any event, system organ class, and preferred term), subjects reporting more than one AE were counted only once.
Abbreviations: MedDRA = Medical Dictionary for Regulatory Activities; TEAE = treatment-emergent adverse event.
[a]Adverse events were coded to system organ class and preferred term using MedDRA, version 24.0.
Adverse events were summarized by number of subjects with AE (percentage) number of occurrences.

TABLE 5

Treatment-Emergent Adverse Events by Preferred Term (Safety Population)

| Preferred Term[a] | Mild (N = 8) | Moderate (N = 8) | Severe (N = 6) | Normal (N = 14) | Overall (N = 36) |
|---|---|---|---|---|---|
| Subjects reporting at least one TEAE | 2 (25.0%) 3 | 2 (25.0%) 4 | 2 (33.3%) 4 | 4 (28.6%) 6 | 10 (27.8%) 17 |
| Diarrhea | 1 (12.5%) 1 | 1 (12.5%) 1 | 1 (16.7%) 1 | 3 (21.4%) 3 | 6 (16.7%) 6 |
| Headache | 0 | 1 (12.5%) 1 | 1 (16.7%) 1 | 0 | 2 (5.6%) 2 |
| Abdominal discomfort | 0 | 0 | 0 | 1 (7.1%) 1 | 1 (2.8%) 1 |
| COVID-19 | 0 | 0 | 1 (16.7%) 1 | 0 | 1 (2.8%) 1 |
| Death | 1 (12.5%) 1 | 0 | 0 | 0 | 1 (2.8%) 1 |
| Epigastric discomfort | 0 | 0 | 0 | 1 (7.1%) 1 | 1 (2.8%) 1 |
| Fatigue | 0 | 1 (12.5%) 1 | 0 | 0 | 1 (2.8%) 1 |
| Haematuria | 1 (12.5%) 1 | 0 | 0 | 0 | 1 (2.8%) 1 |
| Neutropenia | 0 | 0 | 1 (16.7%) 1 | 0 | 1 (2.8%) 1 |
| Pain | 0 | 1 (12.5%) 1 | 0 | 0 | 1 (2.8%) 1 |
| Paraesthesia | 0 | 0 | 0 | 1 (7.1%) 1 | 1 (2.8%) 1 |

Notes:
At each level of summarization (any event, system organ class, and preferred term), subjects reporting more than one AE were counted only once.
Abbreviations: MedDRA = Medical Dictionary for Regulatory Activities; TEAE = treatment-emergent adverse event.
[a]Adverse events were coded to system organ class and preferred term using MedDRA, version 24.0.
Adverse events were summarized by number of subjects with AE (percentage) number of occurrences.

TABLE 6

Related Treatment-Emergent Adverse Events by Preferred Term (Safety Population)

| Preferred Term[a] | Mild (N = 8) | Moderate (N = 8) | Severe (N = 6) | Normal (N = 14) | Overall (N = 36) |
|---|---|---|---|---|---|
| Subjects reporting at least one TEAE | 2 (25.0%) 2 | 2 (25.0%) 4 | 2 (33.3%) 2 | 3 (21.4%) 5 | 9 (25.0%) 13 |
| Diarrhea | 1 (12.5%) 1 | 1 (12.5%) 1 | 1 (16.7%) 1 | 2 (14.3%) 2 | 5 (13.9%) 5 |
| Abdominal discomfort | 0 | 0 | 0 | 1 (7.1%) 1 | 1 (2.8%) 1 |
| Epigastric discomfort | 0 | 0 | 0 | 1 (7.1%) 1 | 1 (2.8%) 1 |
| Fatigue | 0 | 1 (12.5%) 1 | 0 | 0 | 1 (2.8%) 1 |
| Haematuria | 1 (12.5%) 1 | 0 | 0 | 0 | 1 (2.8%) 1 |
| Headache | 0 | 1 (12.5%) 1 | 0 | 0 | 1 (2.8%) 1 |
| Neutropenia | 0 | 0 | 1 (16.7%) 1 | 0 | 1 (2.8%) 1 |
| Pain | 0 | 1 (12.5%) 1 | 0 | 0 | 1 (2.8%) 1 |
| Paraesthesia | 0 | 0 | 0 | 1 (7.1%) 1 | 1 (2.8%) 1 |

Notes:
At each level of summarization (any event and preferred term), subjects reporting more than one adverse event were counted only once. At each level of subject summarization, a subject was classified according to the greatest relationship if the subject reported >1 events. Adverse events with missing relationship were considered related for this summary.
Abbreviations: MedDRA = Medical Dictionary for Regulatory Activities; TEAE = treatment-emergent adverse event.
[a]Adverse events were coded to preferred term using MedDRA, version 24.0. Adverse events were summarized by number of subjects with AE (percentage) number of occurrences.

Overall, 17 TEAEs were experienced by 10 subjects (27.80%). The number of TEAEs reported in the study was similar across all 4 groups. Overall, 9 subjects (25.0%) reported 13 TEAEs that were considered related to paltusotine by the investigator. No subjects discontinued from the study due to a TEAL. All TEALs resolved by the end of the study, except for the TEAL of mild hematuria, which was reported ongoing.

One subject (12.5% o) from the mild hepatic impairment group died due to natural causes on Day 27. The death was considered not related to paltusotine by the investigator.

CONCLUSION

Following single oral administration of 20 mg paltusotine tablets to subjects with varying degrees of hepatic impairment, the peak and total systemic exposures of paltusotine were similar across all hepatic impairment groups when compared to subjects with normal hepatic function. Overall, there were no changes in paltusotine plasma exposure that would be considered clinically meaningful or sufficient to warrant dose adjustment for patients with mild, moderate, or severe hepatic impairment.

Single oral administration of 20 mg paltusotine was safe and generally well tolerated by subjects with varying degrees of hepatic impairment and by subjects with normal hepatic function in this study.

What is claimed is:

1. A method comprising administering a therapeutically effective amount of paltusotine, or a pharmaceutically acceptable salt thereof, to a patient, wherein the patient has hepatic impairment, and wherein the therapeutically effective amount of paltusotine, or a pharmaceutically acceptable salt thereof, is the same amount that would be administered to a patient who does not have hepatic impairment, wherein the paltusotine is administered to the patient to treat acromegaly, carcinoid syndrome and/or neuroendocrine tumor.

2. A method comprising:
  (a) administering to a patient a therapeutically effective amount of paltusotine, or a pharmaceutically acceptable salt thereof;

(b) subsequently determining that the patient has hepatic impairment; and
(c) administering the same therapeutically effective amount of paltusotine, or a pharmaceutically acceptable salt thereof, to the patient without dose adjustment, wherein the paltusotine is administered to the patient to treat acromegaly, carcinoid syndrome and/or neuroendocrine tumor.

3. The method of claim 1, wherein the patient has mild, moderate, or severe hepatic impairment.

4. The method of claim 3, wherein the patient has mild hepatic impairment.

5. The method of claim 3, wherein the patient has moderate hepatic impairment.

6. The method of claim 3, wherein the patient has severe hepatic impairment.

7. The method of claim 1, wherein the patient has a Child-Pugh Score of 5-6, 7-9, or 10-15.

8. The method of claim 7, wherein the patient has a Child-Pugh Score of 4-5.

9. The method of claim 7, wherein the patient has a Child-Pugh Score of 6-8.

10. The method of claim 7, wherein the patient has a Child-Pugh Score of 10-15.

11. The method of claim 1, wherein the patient has acromegaly.

12. The method of claim 11, wherein the paltusotine, or a pharmaceutically acceptable salt thereof, is administered in an amount equivalent to about 40 mg of paltusotine free base.

13. The method of claim 11, wherein the paltusotine, or a pharmaceutically acceptable salt thereof, is administered in an amount equivalent to about 60 mg of paltusotine free base.

14. The method of claim 2, wherein the paltusotine, or a pharmaceutically acceptable salt thereof, is administered to the patient to treat acromegaly.

15. The method of claim 1, wherein the patient has carcinoid syndrome and/or NETs.

16. The method of claim 15, wherein the paltusotine, or a pharmaceutically acceptable salt thereof, is administered in an amount equivalent to about 40 mg of paltusotine free base.

17. The method of claim 15, wherein the paltusotine, or a pharmaceutically acceptable salt thereof, is administered in an amount equivalent to about 80 mg of paltusotine free base.

18. The method of claim 15, wherein the paltusotine, or a pharmaceutically acceptable salt thereof, is administered in an amount equivalent to about 120 mg of paltusotine free base.

19. The method of claim 2, wherein the paltusotine, or a pharmaceutically acceptable salt thereof, is administered to the patient to treat carcinoid syndrome and/or NETs.

20. The method of claim 1, wherein the paltusotine, or a pharmaceutically acceptable salt thereof, is administered daily.

21. The method of claim 1, wherein the paltusotine, or a pharmaceutically acceptable salt thereof, is administered once daily.

22. The method of claim 1, wherein the paltusotine, or a pharmaceutically acceptable salt thereof, is administered orally.

23. The method of claim 1, wherein the paltusotine, or a pharmaceutically acceptable salt thereof, is administered in one or more oral dosage forms.

24. The method of claim 23, wherein the oral dosage form is a tablet.

25. The method of claim 1, wherein the paltusotine, or a pharmaceutically acceptable salt thereof, is a hydrochloride salt of paltusotine.

26. The method of claim 25, wherein the hydrochloride salt of paltusotine is amorphous.

27. The method of claim 1, wherein the patient with hepatic impairment has equivalent exposure of paltusotine free base as in a patient with normal hepatic function who is administered the same amount of paltusotine, or a pharmaceutically acceptable salt thereof.

* * * * *